US008501476B2

(12) United States Patent
Morgan et al.

(10) Patent No.: US 8,501,476 B2
(45) Date of Patent: Aug. 6, 2013

(54) ASSAYS AND METHODS FOR FUSING CELL AGGREGATES TO FORM PROTO-TISSUES

(75) Inventors: Jeffrey R. Morgan, Sharon, MA (US); Dylan Dean, Portland, OR (US); Adam Rago, Falmouth, MA (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 12/896,173

(22) Filed: Oct. 1, 2010

(65) Prior Publication Data

US 2011/0212481 A1 Sep. 1, 2011

Related U.S. Application Data

(60) Provisional application No. 61/249,308, filed on Oct. 7, 2009.

(51) Int. Cl.
*C12N 5/02* (2006.01)

(52) U.S. Cl.
USPC .......................................... 435/395; 435/383

(58) Field of Classification Search
None
See application file for complete search history.

(56) References Cited

U.S. PATENT DOCUMENTS

| | | | |
|---|---|---|---|
| 5,650,164 A | | 7/1997 | Della Valle et al. |
| 7,887,843 B2 * | | 2/2011 | Libera et al. ................... 424/489 |
| 2003/0153078 A1 * | | 8/2003 | Libera et al. ................... 435/383 |
| 2005/0169962 A1 | | 8/2005 | Bhatia et al. |
| 2009/0018033 A1 | | 1/2009 | Morgan et al. |

FOREIGN PATENT DOCUMENTS

| | | |
|---|---|---|
| DE | 4132379 A1 | 4/1993 |
| EP | 1 367 119 | 12/2003 |
| JP | 08-140673 | 6/1996 |
| JP | 2000-069957 | 3/2000 |
| JP | 2003-052361 | 2/2003 |
| JP | 2004-089136 | 3/2004 |
| JP | 2004-097047 | 4/2004 |
| JP | 2004-121168 | 4/2004 |
| JP | 2005160596 | 6/2005 |
| JP | 2006-055069 | 3/2006 |
| WO | WO 95/31184 | 11/1995 |
| WO | WO 99/52356 | 10/1999 |
| WO | WO 03/059072 A1 | 7/2003 |
| WO | WO 2005/077013 | 8/2005 |
| WO | WO 2007/087402 A2 | 8/2007 |

OTHER PUBLICATIONS

Kelm J. M. et al., Tissue-Transplant Fusion and Vascularization of Myocardial Microtissues and Macrotissues Implanted into Chicken Embryos and Rats, Tissue Engineering, 2006, vol. 12, No. 9, pp. 2542-2553.*
Jakab K. et al., Engineering biological structures of prescribed shape using self-assembling multicellular systems, Proceedings of The National Academy of Sciences of the USA (PNAS), Mar. 2, 2004, vol. 101, No. 9, pp. 2864-2869.*
Mironov V. et al., Organ printing: computer-aided jet-based 3D tissue engineering, Trends in Biotechnology, Apr. 2003, vol. 21, No. 4, pp. 157-161.*
Dean, Dylan M., el al., "Rods, tori, and honeycombs: the directed self-assembly of microtissues with prescribed microscale geometries," *The FASEB Journal*, 21:4005-4012 (2007).
Folch, A. and Toner, M., "Microengineering of Cellular Interactions," *Annu. Rev. Biomed. Eng.*, 02:227-256 (2000).
Fukuda, J. and Nakazawa, K., "Orderly Arrangement of Hepatocyte Spheroids on a Microfabricated Chip," *Tissue Engineering*, 11(7/8):1254-1262 (2005).
Kelm, J.M., and Fussenegger, M., "Microscale tissue engineering using gravity-enforced cell assembly," *Trends in Biotechnology*, 22(4):197-202 (2004).
Napolitano, A.P., et al., "Dynamics of the Self-Assembly of Complex Cellular Aggregates on Micromolded Nonadhesive Hydrogels," *Tissue Engineering*, 13(8):2087-2094 (2007).
Napolitano, A.P., et al., "Scaffold-free Three-Dimensional Cell Culture Utilizing Micromolded Nonadhesive Hydrogels," *BioTechniques*, 43:494-500 (2007).
Rago, A.P., et al., "Miniaturization of an Anoikis Assay Using Non-Adhesive Micromolded Hydrogels," *Cytotechnology*, 56:81-90 (2008).
Yeh, J., et al., "Micromolding of Shape-Controlled, Harvestable Cell-Laden Hydrogels," *Biomaterials*, 27:5391-5398 (2006).
English Translation of JP 2006-055069, downloaded from http://www4.ipdl.inpit.go.jp on Nov. 2, 2011.
Livoti, C.M., et al., "Self-Assembly and Tissue Fusion of Toroid-Shaped Minimal Building Units", *Tissue Engineering*, 16(6): 2051-2061 (2010).
Rago, A.P., et al., "Controlling Cell Position in Complex Heterotypic 3D Microtissues by Tissue Fusion", *Biotechnology and Bioengineering*, 102(4): 1231-1241 (Mar. 1, 2009).
Kelm, J.M., et al., "Tissue-Transplant Fusion and Vascularization of Myocardial Microtissues and Macrotissues Implanted into Chicken Embryos and Rats," *Tissue Engineering*, 12(9):2541-2553 (2006).

* cited by examiner

*Primary Examiner* — Jon P Weber
*Assistant Examiner* — Satyendra Singh
(74) *Attorney, Agent, or Firm* — Hamilton, Brook, Smith & Reynolds, P.C.

(57) ABSTRACT

Provided are assays and methods for creating proto-tissues from aggregates of cells. The invention concerns assays and methods useful in tissue engineering and reconstruction techniques, specifically in the formation of macrotissues from microtissues using microtissue pre-culture time as a controlling parameter.

13 Claims, 18 Drawing Sheets
(15 of 18 Drawing Sheet(s) Filed in Color)

ASSAYS AND METHODS FOR FUSING CELL AGGREGATES TO FORM PROTO-TISSUES

RELATED APPLICATION

This application claims the benefit of U.S. Provisional Application No. 61/249,308, filed on Oct. 7, 2009. The entire teachings of the above application(s) is incorporated herein by reference.

GOVERNMENT SUPPORT

This invention was made with government support under the MRSEC Program of the National Science Foundation under award DMR-0520651, the NIRT Program under award DMI-0506661, the National Institutes of Health (NIBIB) grant number R01EB008664-01A1, and the International Foundation for Ethical Research. The government has certain rights in the invention.

BACKGROUND OF THE INVENTION

Tissue fusion and cell sorting are processes fundamental to developmental biology with applications in tissue engineering. Tissue fusion, in which two segregated cell populations come together and interact to generate a single tissue, is common throughout development and includes neural tube formation, skeletal formation and myocardial development. After initial contact, cells can create three-dimensional cavities, tubular structures or higher order structures. Disruptions can lead to significant disorders such as spina bifida and cleft palate. For purposes of tissue engineering, it is important to understand and control tissue fusion because strategies are emerging to use cells and aggregates of cells as building units to create larger, more complex three-dimensional tissue structures. For example, tissue fusion is important in organ printing, a process whereby a modified inkjet printer extrudes small volumes of viable cells or cell aggregates along with extracellular matrix proteins (ECMs) to build a three-dimensional structure layer by layer. See Mironov et al., *Organ printing: computer-aided jet-based three-dimensional tissue engineering*, Trends Biotechnol. 21: 157-61 (2003); Wilson and Boland, *Cell and organ printing 1: protein and cell printers*, Anat Rec A Discov Mol Cell Evol Biol 272: 491-96 (2003); Bolant et al., *Cell and organ printing 2: fusion of cell aggregates in three-dimensional gels*, Anat Rec A Discov Mol Cell Evol Biol 272: 497-502 (2003); Jakab et al., *Engineering biological structures of prescribed shape using self-assembling multicellular systems*, Proc Natl Acad Sci USA 101: 2864-69 (2004). Others are creating microscale modules of cells plus extracellular matrix and assembling these structures to create organoids that can be perfused in vitro. See McGuigan and Sefton, Proc Natl Acad Sci USA 31:11461-114 (2006). Despite its importance, little is understood about the process of tissue fusion and methods are needed to control it. Cell sorting or self-sorting is the ability of two or more cell types to self-organize into distinct regions or layers within a tissue. In development, this process is essential for compartmentalizing cells which leads to neural tube formation, gonad morphogenesis, and development of the heart, lung, and pancreas. Numerous in vitro studies have shown that when two types of mono-dispersed cells are mixed, they will self-assemble a three-dimensional microtissue where one cell type forms the inner core and the other the outer coating of the microtissue. Levels of cell surface adhesion proteins, such as cadherins, influence self-sorting as does cytoskeletal-mediated tension. The ability to control the relative positions of two or more cells within a three-dimensional microtissue has clear applications to tissue engineering. Although much is understood about self-sorting within a single three-dimensional microtissue, there is little understanding of the process when two or more mixed microtissues undergo tissue fusion. Such an event is also important to building larger, more complex tissue structures containing two or more cell types.

A new method for the easy production of large numbers of three-dimensional microtissues (Nap TE and Nap Biotechniques) has been developed and is disclosed in PCT Patent Publication No. WO 2007/087402 published 2 Aug. 2007 (Application No. PCT/US2007/002050 filed 24 Jan. 2007) (see also, Napolitano et al., *Dynamics of the Self-Assembly of Complex Cellular Aggregates on Micromolded Nonadhesive Hydrogels*, Tissue Engineering 12: 2087-94 (2007) and Dean et al., *Rods, tori, and honeycombs: The directed self-assembly of microtissues with prescribed microscale geometries*, FASEB J. 21: 4005-12 (2007)). Briefly, mono-dispersed cells are pipetted onto micro-molded agarose, whereon the cells spontaneously self-assemble three-dimensional microtissues. Microtissue size is controlled by the cell seeding number and mixed microtissues are easily formed by adding a mixture of mono-dispersed cells. Mixed cell suspensions have been seeded into these micro-molded, nonadhesive microgels; the mixed cells segregate into types, with one cell type surrounding the other. Id. Other techniques for aggregating cells are disclosed and reviewed Lin and Chang, *Recent advances in three-dimensional multicellular spheroid culture for biomedical research*, Biotechnol. J. 3: 1013 (2008).

There is a need in tissue engineering to understand the dynamics and factors governing the fusion of microtissues and the cell sorting that occurs after fusion. The current invention is directed to this aspect of the field.

SUMMARY OF THE INVENTION

The invention is generally directed to assays and methods useful in tissue engineering and reconstruction techniques. It forwards the development of microtissues and macrotissues for use in artificial tissue implants for regenerative medicine.

In one aspect, the invention is an assay for assessing the parameters affecting macrotissue formation from microtissue fusion comprising the steps of (1) pre-culturing at least two microtissues; (2) placing the pre-cultured microtissues onto a surface of a substrate that is nonadhesive in the area in which tissue fusion is desired so as to effect contact between the microtissues; (3) maintaining the microtissues on the surface of the substrate; and (4) determining the parameters necessary for the function and usefulness of the resultant macrotissue.

In another aspect, the invention is a method of forming a macrotissue having desired cell sorting characteristics and cell position from at least two different microtissues comprising the steps of (1) pre-culturing the microtissues; (2) placing the pre-cultured microtissues onto a surface of a substrate that is nonadhesive in the area in which tissue fusion is desired so as to effect contact between the microtissues; and (3) maintaining the microtissues on the surface of the substrate until the desired macrotissue is formed, wherein pre-culture time is varied in order to influence cell position within the macrotissue.

In yet another aspect, the invention is a method of controlling the formation of macrotissues from at least two microtissues comprising the steps of (1) separately pre-culturing the microtissues for one hour to seven days; (2) thereafter, placing the pre-cultured microtissues onto a surface of a substrate that is nonadhesive in the area in which tissue fusion is desired so as to effect contact between the microtissues; (3) maintaining the microtissues on the surface of the substrate for a period of time until a macrotissue has formed; and (4) harvesting the macrotissue. In these methods, the rate and extent of fusion is controlled by limiting pre-culture time. Because the rate and extent of fusion varies inversely with length of pre-culture time, the shorter the pre-culture time, the faster the fusion to form macrotissue proceeds and the greater the extent of fusion. The microtissues may be of the same or of different cell types. It has been determined that when microtissues of different cell types are pre-cultured prior to fusion, the cells maintain their position and aggregate shape within the resulting macrotissue. Therefore, this method may find particular utility in the formation of macrotissues employable in tissue reconstruction and tissue engineering techniques.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figures 1A, 1B, 1C, 1D, 1E, 1F:
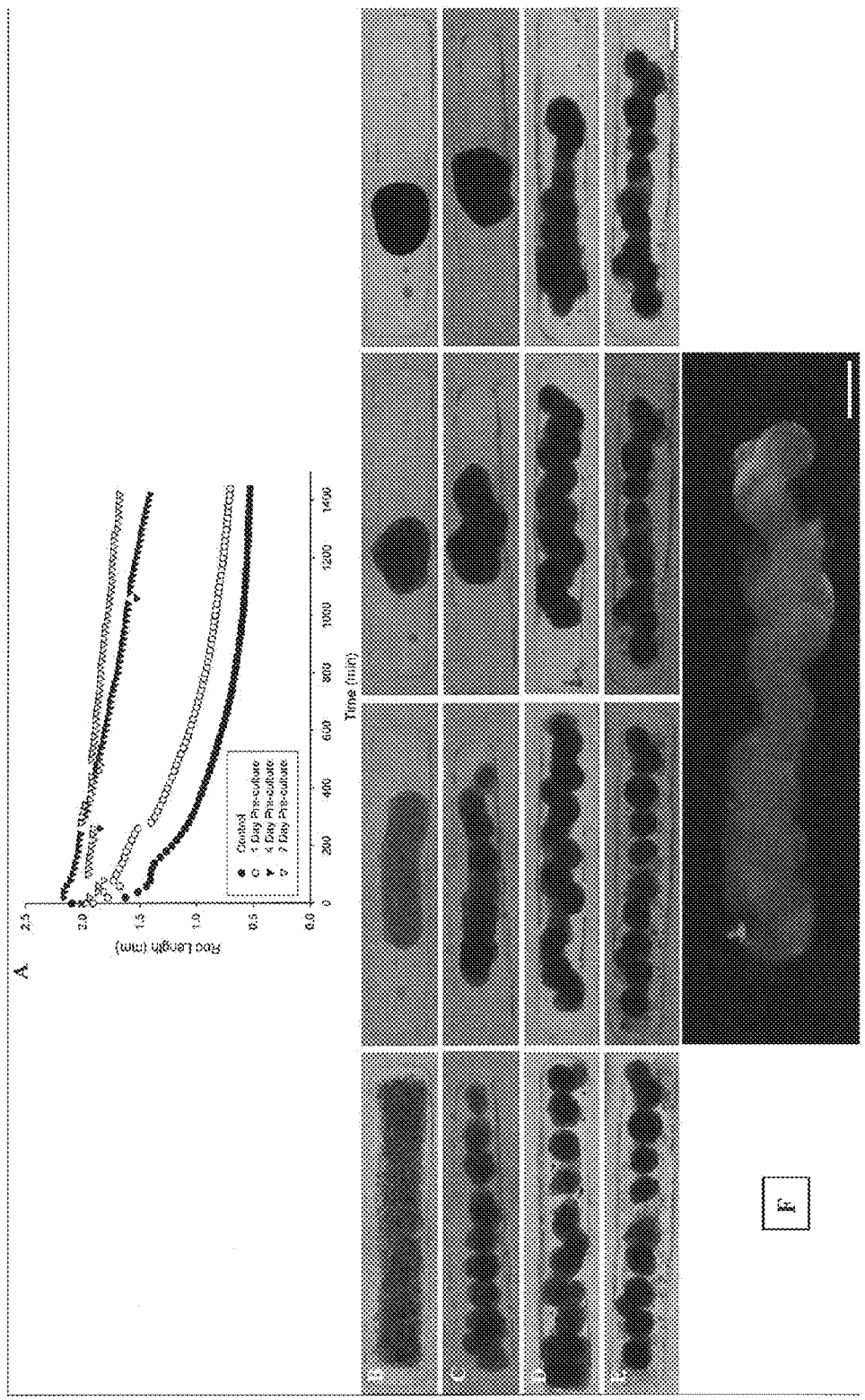
FIGS. 1A-1F: Kinetics of microtissue assembly and steady-state length can be controlled by varying pre-culture time of large microtissue building units. Microtissues (300 μm diameter) were cultured for one (open circles), four (closed triangles), or seven (open triangles), then seeded into a mold containing trough recesses and allowed to fuse for 24 hours. Rod length is plotted as a function of fusion time (A). Representative images at zero, three, twelve, and twenty-four hours are shown for monodispersed cells (B), one day (C), four day (D) and seven day pre-cultured microtissues (E). Fused microtissues were stained for viability using a live/dead assay after seven days of pre-culture (F). Scale bars are 200 μm.
Figures 2A, 2B, 2C, 2D, 2E:
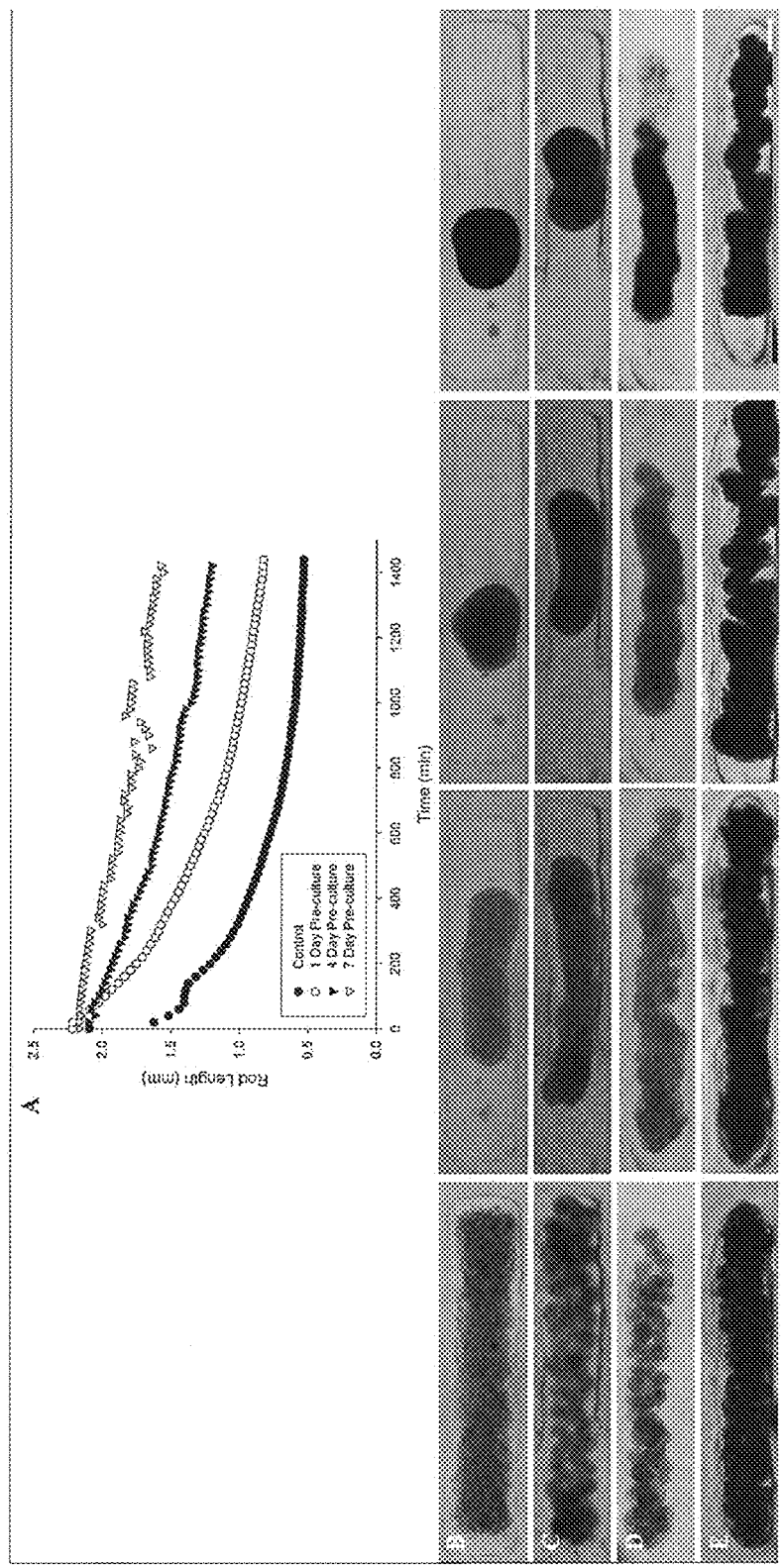
FIGS. 2A-2E: Kinetics of microtissue assembly and steady-state length can be controlled by varying pre-culture time of small spheroid building units. Microtissues (about 100 μm diameter) were cultured for one (open circles), four (closed triangles), or seven (open triangles), then seeded into a mold containing trough recesses and allowed to fuse for 24 hours. Rod length is plotted as a function of fusion time (A). Representative images at zero, three, twelve, and twenty-four hours are shown for monodispersed cells (B), one day (C), four day (D) and seven day pre-cultured microtissues (E). Scale bar is 200 μm.

In an embodiment, the invention is an assay method for assessing the parameters affecting macrotissue formation from microtissue fusion. The assay method includes the steps of pre-culturing at least two microtissues; (b) placing the pre-cultured microtissues onto a surface of a substrate that is nonadhesive in an area in which tissue fusion is desired so as to effect contact between the microtissues; (c) maintaining the microtissues on the surface of the substrate; and (d) determining the parameters necessary for the function and usefulness of the resultant macrotissue.

In another embodiment, the invention is a method of forming a macrotissue having desired cell sorting characteristics and cell position from at least two different microtissues that comprising the steps of pre-culturing the microtissues; placing the pre-cultured microtissues onto a surface of a substrate that is nonadhesive in the area in which tissue fusion is desired so as to effect contact between the microtissues; and (c) maintaining the microtissues on the surface of the substrate until the desired macrotissue is formed, wherein pre-culture time is varied in order to influence cell position with the macrotissue.

In an additional embodiment, the invention is a method of controlling the formation of macrotissues from at least two microtissues comprising the steps of separately pre-culturing the microtissues for about one hour to about fourteen days; (b) thereafter, placing the pre-cultured microtissues onto the surface of a substrate that is nonadhesive in the area in which tissue fusion is desired so as to effect contact between the microtissues; (c) maintaining the microtissues on the surface of the substrate for a period of time until a macrotissue has formed; and (d) harvesting the macrotissue.

The microtissues employed in the methods of the invention can be separately cultured for about one hour to about fourteen days, for example, a one hour, about 2 hours, about 4 hours, about 8 hours, about 24 hours, about 1 days, about 2 days, about 4 days, about 6 days, about 7 days, about 8 days, about 10 days, about 12 days and about 14 days. In another embodiment, the microtissues employed in the methods of the invention can be separately precultured for about 1 week, about 2 weeks, about 3 weeks, about 4 weeks, about 6 weeks, about 8 weeks, about 10 weeks, about 12 weeks, about 14 weeks and about 16 weeks.

A significant challenge of tissue engineering is to build tissues whose size is not limited by diffusion. The use of scaffold-free, lumen-containing, toroid-shaped microtissues as minimal building units for large, porous three-dimensional tissues with high cell density is reported herein. Mono-dispersed H35 cells, a rat hepatocyte cell line, were seeded onto micro-molded agarose, forming self-assembled multi-cellular toroids within 48 hours. Toroid and lumen diameter were easily controlled by micro-mold design, and toroid thickness was controlled by seeding density. When harvested, toroids were stable, but underwent predictable changes over time with their lumens narrowing. When brought into contact, these building units fused in the x-y plane, forming a double-lumen structure, as well as in the z plane, forming a tubular structure, within 72 hours. Large, multi-luminal structures were assembled by multi-dimensional fusion of many toroids. Toroid settling was not entirely random, with most toroids lying flat with their lumens oriented along the z axis. The rapid production of toroid building units of controlled dimension and lumen size that undergo predictable changes and that can be fused to form larger structures is a significant step in the engineering of large, porous three-dimensional tissues with high cell density.

A major challenge to tissue engineering is the in vitro fabrication of large tissue constructs with high densities of living cells, similar to natural organs and tissues (1, 2). Hurdles are numerous, notably that the diffusion of oxygen, nutrients and metabolic waste products limits cellular tissues to thicknesses of about 100-200 μm in order to maintain viability (3, 4). In natural organs and tissues, a branching vascular supply ensures all cells are close to blood vessels (1, 5). Tissue engineering approaches to this problem have included efforts to make an artificial vascular tree by microfabrication of degradable polymers (6), the assembly of modules of cells and collagen (7-10) and the layer-by-layer printing of cells and extracellular matrix like materials (11-16).

A versatile approach to forming multi-cellular microtissues of defined sizes and geometries (17, 18) is reported herein. Mono-dispersed cells seeded onto micro-molds of agarose settle into the small recesses, where they are unable to attach to the agarose, allowing cell-to-cell adhesion to direct cells to aggregate and self-assemble a three-dimensional multi-cellular microtissue. This occurs in the absence of any added scaffold or extracellular matrix protein and is complete within 24-48 hours. The shape of the microtissue is controlled by the shape of the recesses that are micro-molded into the agarose. It had been thought that cells would self-assemble only a spheroid, in which surface area and surface free energy are minimized. However, the use of agarose micro-molds to direct the self-assembly of complex shapes such as toroids is reported herein (17, 18).

The toroid building unit, with its ring of cells in high density and open lumen space, offers interesting possibilities for building a large tissue construct with both a high cell density and a network of interconnected lumens. Toroid and lumen diameters are easily controlled by micro-mold design, and toroid thickness is controlled by the number of mono-dispersed cells seeded. When harvested, the toroids are intact and undergo predictable changes to their size and shape over time. Moreover, toroids can fuse with one another in a process that is complete within 72 hours and toroids can be used as building units to make a large, multi-layered, multi-torus structure.

Most successful tissue engineering applications have used thin tissues (<2 mm), in which transport of oxygen, nutrients, and metabolic waste critical for cell viability occurs by diffusion (1). In highly cellular tissues, this distance is thought to be about 100-200 microns, challenging the field of tissue engineering to design large tissue constructs that are, or can become vascularized (3, 20). The present invention presents data on the self-assembly and stability of a scaffold-free cellular toroid and its use as a building unit.

Scaffold-free cellular microtissues in the shape of spheroids have been described (12). For example, spheroids of Chinese hamster ovary cells (about 500 μm diameter) prepared by extruding a larger cell pellet through a capillary tube were harvested and added to a ring shaped mold of collagen gel. After 4-5 days, the spheroids fused to form a single large toroid (about 2.3 mm diameter) and cells in the spheroids adhered to and migrated into the surrounding collagen gel. A hanging drop method has been described to prepare smaller spheroids of myoblasts or chondrocytes and fused them to make large macrotissue patches (mm sized) (21). Likewise, spheroids of myofibroblasts, coated with human umbilical vein endothelial cells (HUVEC), have been fused and formed a capillary network within the macrotissue that could connect to the host vasculature after transplantation (21). As described herein, spheroids are prepared in micro-molded agarose as building units to control cell position, and to form small toroidal and honeycomb shaped structures (19).

Scaffolds have been described as part of a biofabrication or bioprinting approach (11, 13-16). This approach is a modification of ink jet printing or rapid prototyping technologies, with tissue constructs made layer-by-layer by printing mono-dispersed cells or spheroids along with an extracellular matrix-like material. Computer control of the deposition process facilitates the fabrication of large complex shaped structures. In another scaffold based approach, cells are cast within small (submillimeter) gels and these are used as building units (7-10). HepG2, a human hepatoma cell line, were encapsulated in cylindrical collagen gels and the capsules were subsequently coated with HUVECs. These building units were packed into a larger vessel where they created a luminal network via the space between the building units, with the endothelial cells reducing thrombogenicity when the construct was perfused with blood in vitro (7-10). Another group has shown that the shape of cell-containing microgels can help direct the assembly of these building units and their orientations (22).

Described herein is the use of agarose micro-molds to direct the self-assembly of mono-dispersed cells into toroidal shaped multi-cellular microtissues and the demonstration of these scaffold-free toxoids as building units to form larger tissue structures by the process of tissue fusion. Further, lumen and toroid size can be easily controlled, and their fusion proceeds with predictable kinetics. Unlike the spheroid shape, where diffusion limits its maximum size, toroid building units can be made over a range of diameters without compromising cell viability, provided the thickness of the tissue does not exceed the diffusion limit. The fundamental shape of a toroid, with its open lumen structure, provides new possibilities as a building unit that, when fused, can produce dense cellular tissues with a network of interconnected lumens.

There are straightforward ways to control the size of the toroid and its lumen. The first step is the design of the micro-mold. Micro-molds, where cells self-assembled toroids with lumens, can range in diameter from about 1000 μm down to about 400 μm. Self-assembly by mono-dispersed cells is rapid and occurs within 48 hours. Lumen size is controlled by the diameter of the agarose peg in the micro-mold. Technologies, such as photolithography, can be used to make molds with smaller pegs that could create toroids with even smaller lumens.

Thickness of the toroid can be controlled by the number of mono-dispersed cells seeded into the micro-molds. After seeding, the cells self-assemble and contract around the peg forming the toroidal shaped microtissue. The x, y thickness can be varied from about 250 μm to about 600 μm after four days of self-assembly (FIG. 13), depending on the number of cells seeded. There are a minimal number of cells needed to form a toroid which is probably dependent on cell type and mold design. In some embodiments of the present invention, the number of cells is in the range of about 5-10 cells per micron of circumference of the peg.

Once released from the micro-molds, the toroids remained intact, but underwent predictable changes to their size and shape. These changes are mediated by cellular processes and an understanding of the types of changes that occur as well as their kinetics provides another level of control over the size and shape of the toroid building unit. After release from the micro-mold, the lumen diameter of the 600 μm toroid narrowed to a minimum of about 100 μm after about 10 days, while its outer diameter decreased by only 6%. The largest change in lumen diameter (44%) occurred within the first 24 hours and is probably due to the release of cellular tension built up as the toroid contracts around the peg. These forces of self-assembly involve not only cell surface adhesion molecules, but also the action of the cytoskeleton (23, 24).

The toroid's lumen undergoes significant narrowing, but changes to its outer diameter are minimal due to the fact that the toroid's x, y thickness increases. When first harvested, the z dimension of about 600 μm toroid was about 113.6+/−21.2 μm and the thickness in the x, y dimensions was about 246.3+/−26.8 μm. Over ten days, the x, y thickness increased steadily to a maximum of about 479.2+/−23.6 μm. This thickening may be due to cellular migration and spreading of the toroid and/or cell proliferation. It is interesting to note that the rate of thickening was nearly the same for the 600 μm and the 1000 μm toroids, suggesting that the process is independent of toroid diameter. Cell density in the toroid was initially uniform, but with time, cell density increased in a non-uniform way with high cell density localized to a central ring closer to the lumen rather than the outermost circumference.

Toroids can be about 21,000 cells in a diameter of about 600 to about 800 μm, which can be considered subunits that can be used to produce a particular geometry, in which case the toriods would include multiple subunits.

Critical to the usefulness of a building unit is its ability to be used to build larger structures. In biofabrication, spheroids, along with an extracellular matrix-like material, are melded together to build a tissue; the toroids of the present invention can be useful in this approach. Scaffold-free building units, such as spheroids, can also undergo cell mediated fusion to build larger structures (12, 19, 25). Toroids can fuse at points of contact along their outer rim as well as their top and bottom surfaces. The kinetics of fusion shows that this process is largely complete after 48 to 72 hours with some compaction when fusion occurs along the top and bottom surfaces. Similar to spheroid fusion, fluorescently labeled toroids show that fusion occurs with minimal cell mixing between the building units (25). Cell-cell adhesion is critical to fusion (26), and surface adhesion molecules, such as cadherins and integrins, are involved as well as the cytoskeleton to which these proteins are linked (27).

The toroids of the present invention can be fused to form large, multi-torus structures. Toroids were added to a single well and allowed to settle to form a random pile of toroids; however, the settling was not random. Overlap of toroids was random, but the majority of toroids had their lumens oriented along the z axis. This bias is probably due to the shape of the toroid and would provide a dominant orientation to the network of lumens created after fusion. Moreover, toroids that are randomly overlapped would create a range of lumen sizes after fusion, all smaller than the lumen of the building unit. This approach can be useful for mimicking the range of vessels that connect capillaries to small diameter arteries and veins (about 0.1-5.0 mm) (28).

It is possible to make toroids with two or more different cell types. When two cell types are mixed and added to micromolds, the cells self-assemble a mixed-cell toroid (18). The cells also self-sorted so that one cell type was located in the inner core of the toroid and the other cell type formed an outer coating. A self-sorting phenomenon has been observed in spheroids and patterns vary with cell types (29, 30). Another variation on the toroid building unit is a larger structure with multiple lumens. Cells can also self-assemble a stable honeycomb structure with thirteen lumens (18, 31). Like toroids, these honeycomb parts self-assemble within forty-eight hours and could be fused with other parts in a similar time frame. Parts of different sizes, geometries and cell types could be mixed or directed by secondary molds to control the size, shape, cell position and lumen sizes of a large tissue construct.

Little is understood about tissue fusion and self-sorting that occurs after heterotypic microtissues are fused. Although common in development, few in vitro methods exist for the quantitative study of these processes and methods are needed to control them for applications in tissue engineering.

To understand the parameters controlling tissue fusion, a simple, versatile, and straightforward assay to quantify tissue fusion was devised and used to investigate the factors controlling fusion and cell sorting. In this assay, preformed microtissues were seeded into a micro-molded agarose gel with trough recesses at a high enough density that they fill the trough, contact each other and undergo tissue fusion. Because the microtissues are arranged in a linear trough, the kinetics and extent of microtissue fusion is easily quantified by measuring the change in long axis of the rod microtissue they form as result of their fusion (rod contraction). The results of the experiments detailed below indicate that pre-culture time has a significant effect on the rate of fusion and the extent of fusion and that, surprisingly, microtissue size is an insignificant factor. With respect to pre-culture time, rate and extent of fusion varied inversely with length of pre-culture time. Also, unexpectedly, it was found that when mixed-cell microtissues were pre-cultured prior to fusion, cells maintained their position and aggregate shape within a fused microtissue.

The assay finds utility in the study of factors controlling microtissue fusion and the self-sorting that occurs when mixed microtissues are fused and in the production of fused microtissues. Spheroid shaped microtissues were harvested from micromolds and subsequently seeded onto new micromolds having trough features formed and arranged so that the microtissues contact one another and undergo fusion. Fusion was quantified by measuring the contraction of the rod-like structure formed by the fusing microtissues.

Spheroid microtissues are simply pipetted into trough features of a micromolded agarose gel where they underwent fusion which could be quantified by measuring rod contraction. The troughs facilitated the contact between microtissues needed for fusion and the troughs also set the initial conditions of fusion by arranging microtissues in a linear array forcing them to fuse in a rod-like structure whose length could be easily quantified by time-lapse microscopy. In addition, since agarose is nonadhesive for cells, cell-to-cell interactions that drive tissue fusion predominate. This is in contrast to other assays where fusion occurs when microtissues are embedded in an adhesive environment (e.g., collagen gel), where cell-to-ECM interactions influence the process and have been shown to disassemble microtissues (earlier reference cited in Nap TE on toroids).

Using this assay, it was possible to investigate numerous factors controlling fusion and pre-culture time of the microtissue prior to fusion had the most significant effect. Using NHF microtissues, the rate of fusion slowed and the steady-state length of the fused rod increased as microtissue pre-culture time was increased. Microtissues pre-cultured for 7 days prior to fusion had the slowest rate of fusion and resulted in the longest rod at 24 hours. As pre-culture time was shortened from 4 days to 1 day, and to no pre-culture (mono-dispersed cells), the rate of fusion increased and rod length decreased. In fact, mono-dispersed cells contracted at an exponential rate and formed a spherical microtissue, whereas microtissues pre-cultured for 7 days contracted at a linear rate and formed a long rod structure. All microtissues reached an approximate steady-state after 24 hours, which did not change in length after four days of culture. These differences were also evident when the fusion angle between microtissue units was measured. The fusion angle decreased and individual microtissue units were more discernible as pre-culture time increased from about 1 to about 7 days. Thus, at the level of individual microtissue units, it was also apparent that fusion was reduced by increased pre-culture time.

Numerous factors could explain why fusion was reduced with pre-culture time. Because the number of cells seeded into each trough was held constant (about $3.0 \times 10^4$ cells/trough) for mono-dispersed cells and for microtissues, differences in cell number was ruled out as a possible cause. Difference in cell viability was also ruled out because our live/dead assay demonstrated that cell viability was high, even after seven days of culture and subsequent assembly. Without being bound by theory, the most likely explanation is that the microtissues change from a more liquid state to a more viscoelastic state as they are pre-cultured. This transformation could result from a number of factors including the production of endogenous ECM proteins, the maturation of cell-to-cell contacts as well as cell-to-ECM contacts and the inhibition of cell motility.

One surprising finding was that there were no significant differences between small and large microtissues in the fusion assay. Both were equally influenced by pre-culture time, but there were no differences in the rate of rod contraction, or the steady-state length of the rods. Contact between microtissues is essential for tissue fusion, and therefore the reactive surface area of the building units is of interest. Mathematical modeling suggests that surface area is inversely related to microtissue stability: the greater the surface area, the higher the free energy of the system. See Glazier et al., *Simulation of the differential adhesion driven rearrangement of biological cells, Phys Rev E* 47: 2128-2154 (1993). Therefore, microtissue shapes and sizes with more surface area might be expected to react more quickly to reduce their overall free energy, however this was not the case for small versus large microtissues. In each well, it was estimated that the surface area was about $5.0 \times 10^6$ $\mu m^2$ for small microtissues and about $2.5 \times 10^6$ $\mu m^2$ for large microtissues, an increase of a factor of two. For comparison, mono-dispersed cells had an approximate surface area of about $3.8 \times 10^7$ $\mu m^2$, an increase of a factor of about 7.6 and 15.2 for small and large microtissues, respectively. Another factor that might be expected to increase the reactivity of small microtissues is the fact that they were packed in three-dimensions and so had numerous contacts with neighboring microtissues, whereas large microtissues contacted only two neighboring microtissues. Nevertheless, no differences were seen in the reactivity of small versus large microtissues. Pre-culture for the one day can optionally be added to form the microtissues overrides the difference in surface area.

Figures 9A, 9B, 9C, 9D, 9E:
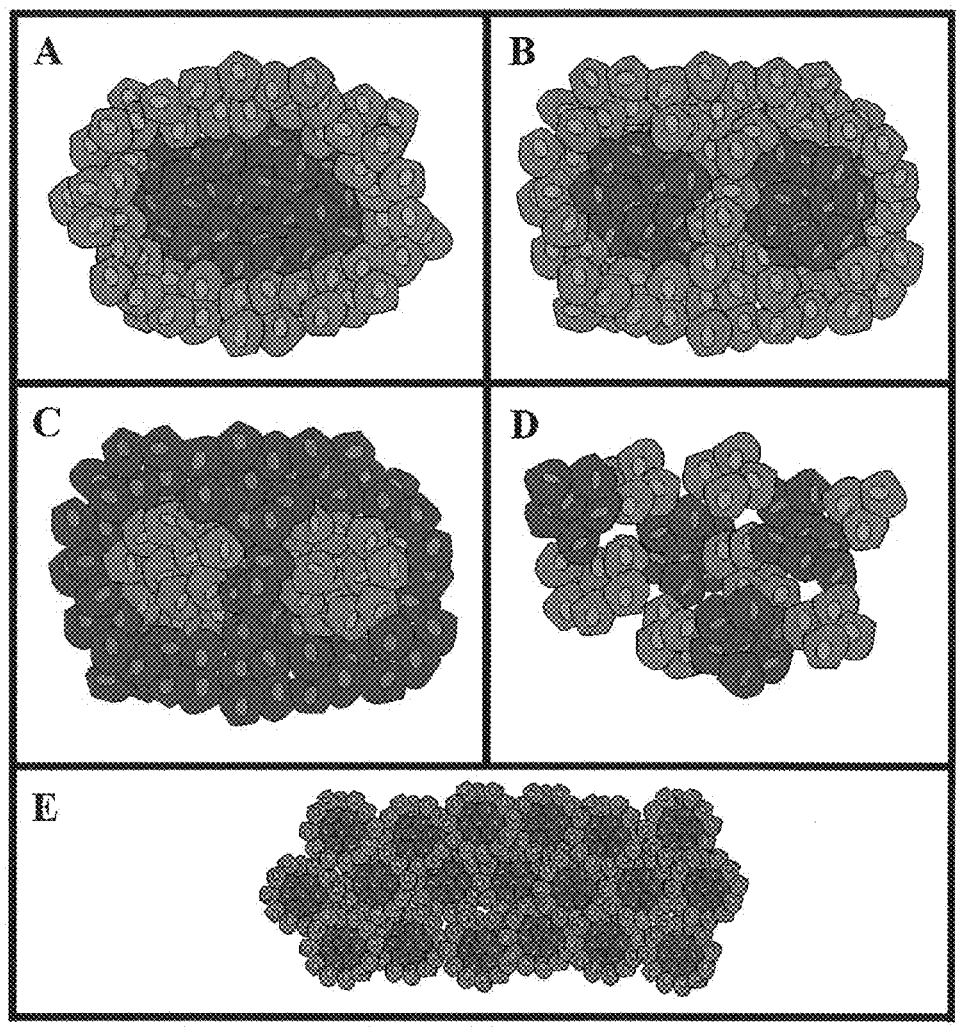
FIGS. 9A-9E: Schematic representation of microtissues that can be generated by controlling the pre-culture time of the building unit before assembly: (A) core-coating; (B) separate, but completely engulfed; (C) inside-out; (D) random unengulfed; (E) individually coated spheroids.
Figures 10A, 10B, 10C, 10D, 10E, 10F, 10G, 10H, 10I, 10J:
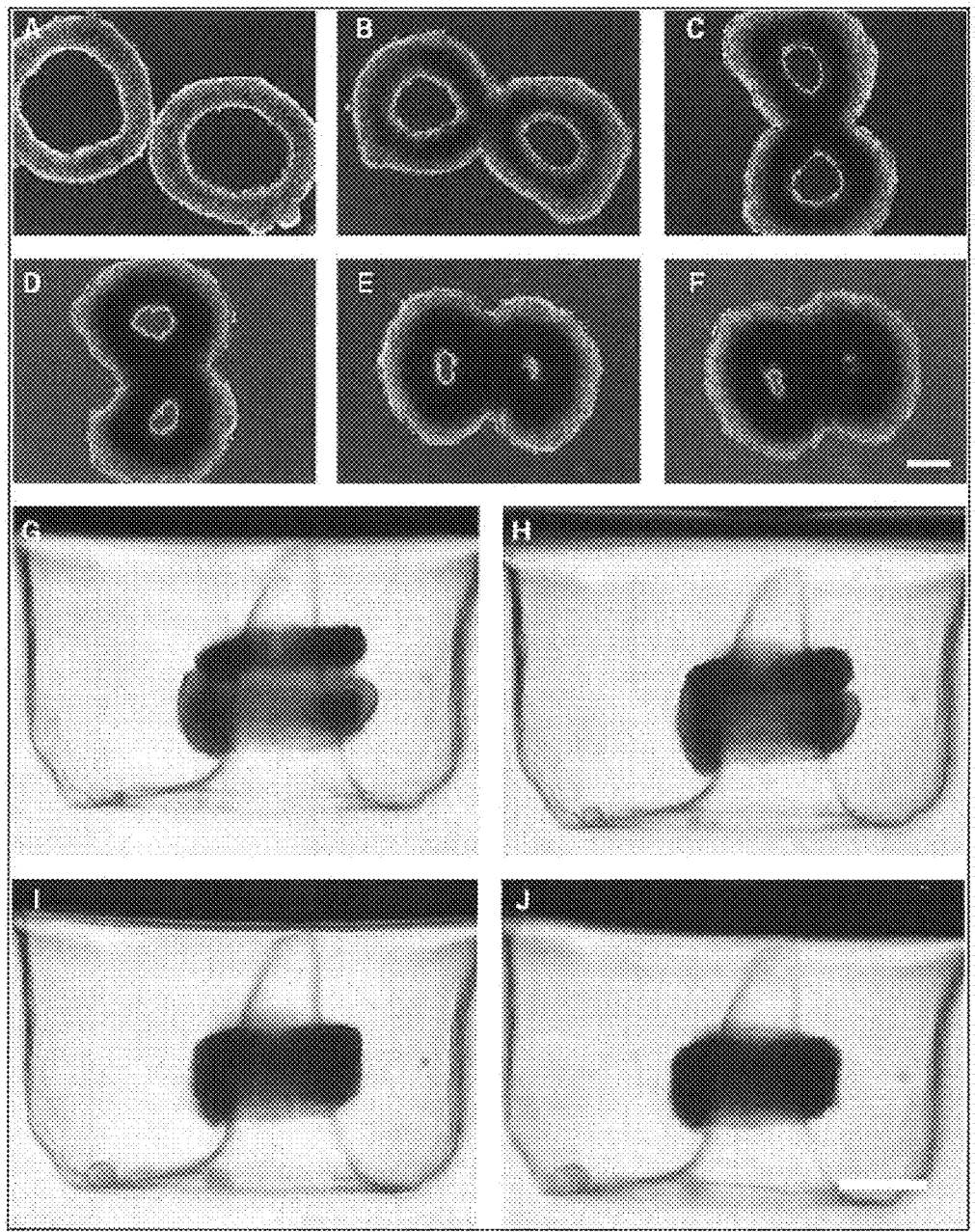
FIGS. 10A-10J: Toroids undergo fusion in multiple dimensions. Toroids were self-assembled and culture for 48 hours prior to being harvested and tested for fusion. Two toroids placed apposed to one another on flat, non-adhesive agarose fused in the x-y plane into a double-lumen structure. Bright-field images at days 0, 2, 4, 6, 8, and 10 are shown (A-F). A harvested toroid was stacked onto another that had previously self-assembled on a non-adhesive conical peg. Both toroids fused in the z plane. Bright-field side view images at 0, 24, 48, and 72 hours are shown (G-J). Scale bar is 200 μm.
Figures 11A, 11B, 11C, 11D, 11E, 11F:
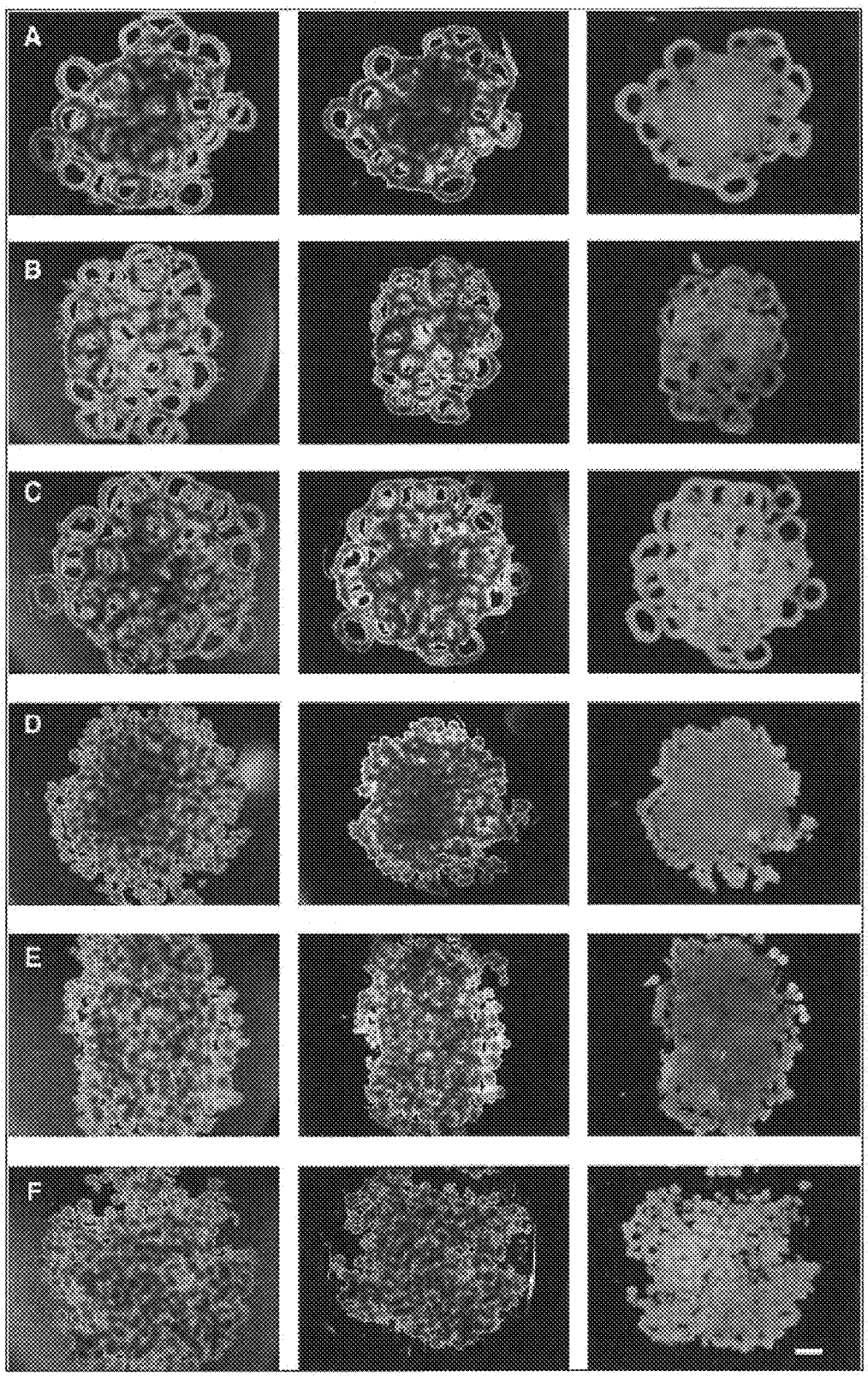
FIGS. 11A-11F: Toroids will fuse to form large, multi-luminal structures. Toroids (A-C) (about 75 toroids, about 600 μm) or spheroids (D-F) (about 800 toroids, about 200 μm) were harvested after 48 hours of self-assembly and added to a single large well cast in agarose. The microtissues settled and formed a pile at the bottom of the well at day 0 (left column). Toroids overlapped randomly but their lumens were oriented along the z axis. After 7 days (center column), samples were stained for viability with a live-dead assay (right column), which revealed higher proportions of viable cells (green) than dead cells (red) in toroid samples, as compared to spheroid samples. Scale bar is 500 μm.
Figures 12A, 12B, 12C, 12D:
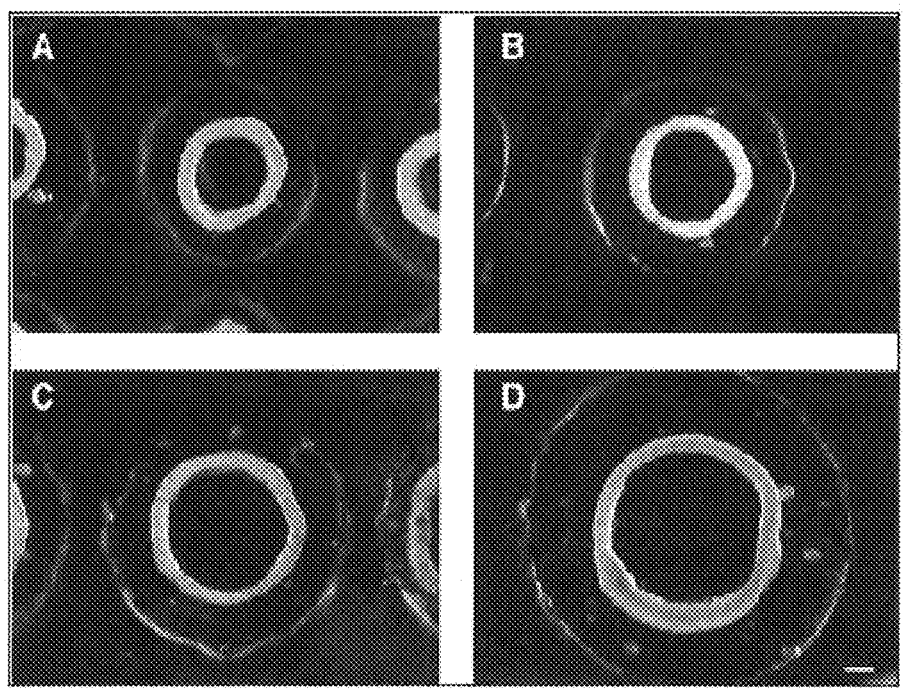
FIGS. 12A-12D: Toroid diameter and lumen diameter can be controlled by micro-mold design. Mono-dispersed cells ($2 \times 10^6$) were seeded onto agarose micro-molds containing toroidal shaped recesses of varying dimensions. The width of the circular tracks were the same (about 400 μm), but the diameter of the peg varied, about 400, about 600, about 800, or about 1000 μm (A-D). Forty eight hours after seeding, mono-dispersed cells self-assembled multi-cellular toroids that contracted around the peg. Scale bar is 200 μm.

The assay was also employed to investigate the cell sorting that occurs after two heterotypic microtissues are fused. In single unfused microtissues, sorting of cell types has been described by the differential adhesion hypothesis (DAH), a theory that suggests that cell types behave like immiscible fluids and self-sort due to differences in cell-cell adhesion and cohesion. See Steinberg, *Mechanism of tissue reconstruction by dissociated cell. II. Time-course of events, Science* 137: 762-63 (1962), The DAH is predicated on a series of assumptions: that cells are discrete units, that cells are mobile, and that different cell types are differentially adhesive and cohesive. See Foty and Steinbers, *The differential adhesion hypothesis: a direct evaluation, Dev Biol.* 278: 255-63 (2005). Mixing of mono-dispersed NHFs and H35s resulted in a microtissue consistent with DAH predictions. NHFs with greater cohesiveness formed a core that was coated by H35s. Whereas the DAH would predict that all NHF—H35 mixes should result in an NHF core surrounded by H35s, we showed that pre-culture time could be used to control cell position. When microtissues were pre-cultured prior to fusion, cells maintained their position and aggregate shape within a fused microtissue. The same phenomenon was evidenced by the increase in fusion angle in NHF assembly experiments. Sorting of one day pre-cultured spheroids were similar to mono-dispersed cells, but differed significantly when microtissues were pre-cultured for four and seven days. By varying pre-culture, at least five distinct archetypal structures were generated and are shown schematically in FIGS. 9A-9E with red cells representing NHFs and green cells representing H35s. Using NHFs and H35s as model cell types, the following organizations can be prescribed: core-coating (FIG. 9A), separate, but completely engulfed (FIG. 9B), inside-out (FIG. 9C), random unengulfed (FIG. 9D), and individually coated NHF spheres (FIG. 9E). The same factors controlling the rate and extent of fusion may also be controlling cell sorting when microtissues are pre-cultured, including endogenous ECM, maturation of cell-to-cell contacts as well as cell-to-ECM contacts and the inhibition of cell motility.

These archetypal structures and the ability to control cell position may be important for future tissue engineering applications. Spatially arranged clusters of different cell types are reminiscent of endocrine tissue architecture in vivo. For instance, four cell types, including alpha and beta cells, are clustered within functionally distinct regions in the Islets of Langerhans. Using cells differentiated from stem cells, it should be possible to reproduce the optimal arrangement of cell types within a mixed microtissue for use in pancreatic replacement therapy. Additionally, the ovarian follicle consists of an oocyte surrounded by layers of granulosa cells and theca cells. Simulating this organization using tissue fusion may also be useful in artificial oogenesis. Methods to date for controlling cell sorting have relied on genetic modification strategies such as upregulation of cadherin levels. The use of pre-culture time and a tissue fusion strategy to control cell position within a complex microtissue offers a more clinically acceptable approach.

Multiple groups have proposed using cells and aggregates of cells along with ECM proteins as building blocks in organ building strategies based on inkjet printer technology (see Jakab et al., *Tissue Engineering by Self-Assembly of Cells Printed into Topologically Defined Structures, Tissue Eng. Part A* 14: 413-21 (Mar. 1, 2008); Smith et al., *Three-dimensional bioassembly tool for generating viable tissue-engineered constructs, Tissue Eng.* 10: 1566-76 (2004); Mironov, supra.) or based on simple packing and endothelialization of preformed collagen gel-cell modules (see Sefton and McGuigan, United States Patent Publication 2003/0228290 published 11 Dec. 2003). Understanding and controlling tissue fusion and cell sorting is important for these strategies as they seek to build vascularized organs with complex shapes and multiple cell types. Use of pre-formed microtissues that undergo fusion may be advantageous relative to individual cells for several reasons. Microtissues may be better able to preserve their viability during handling procedures, microtissues already have a high cell density approximating that of native tissue, and microtissues create an immediate three dimensional structure upon assembly, thus reducing the time necessary to create a structure. See Jakab 2004, supra. Further, structures made from fused myofibroblast/endothelial cell microtissues displayed different histological organization relative to those constructed from mono-dispersed cells (see Kelm et al., *Design of custom-shaped vascularized tissues using microtissue spheroids as minimal building units, Tissue Eng.* 12: 2151-60 (2006)), suggesting that three-dimensional building units can create novel structures. Lastly, it has recently been shown that the shape of microtissues self-assembled from mono-dispersed cells is not limited to a spherical geometry, the shape that minimizes surface area; rather, complex lumen-containing shapes, such as toroids and honeycombs, can be self-assembled from mono-dispersed cells or from preformed microtissues. Thus, microtissues with these shapes can also be used in building strategies in conjunction with an understanding of fusion and cell sorting.

In the assay, normal human fibroblast (NHF) spheroids, used as an exemplary tissue type, were self-assembled and cultured for one, four, or seven days, then combined in trough shaped recesses. Over a 24-hour period, the spheroids fused to become a rod shaped microtissue and the kinetics and extent of fusion was quantified by assessing rod contraction. By varying the amount of spheroid culture time prior to fusion (1 to 7 days), the rate of fusion, the coherence of the building units (as measured by fusion angle) and the steady-state length of the structure could be easily controlled. Longer pre-culture times for the spheroids resulted in slower fusion, less coherence and increased length of rod microtissues. The fusion kinetics and steady-state length of rods formed by smaller versus larger spheroids (about 100 vs about 300 μm diameter) were indistinguishable, even though smaller spheroids had twice the surface area and greater numbers of contacts between units. Both small and large spheroids were strongly influenced by spheroid pre-culture time. Pre-culture time could also be used to control cell sorting and cell position when combinations of NHFs and H35s, a rat hepatocyte cell line, were fused to form heterotypic microtissues. Control of fusion and cell position are important parameters for creating functional heterotypic microtissues as well as the use of microtissues as building units to create larger tissue structures. In sum, pre-culture time and/or microtissue maturity influence the rate and extent of contraction and can be used to control tissue fusion as well as cell position when mixed microtissues are fused.

With regard to pre-culture time these results show that pre-culture of microtissues slows the rate and extent of fusion when microtissues are combined. This is desirable because it affords control over the process of macrotissue formation and tissue reconstruction. When monodispersed cells (no pre-culture time) are seeded into a trough and they "fuse" with one another, they rapidly contract and form a spheroid. In contrast, if the same cells are formed into spheroids before fusion and pre-cultured, the microtissue "contraction" (i.e., fusion of these microtissues) is slower and the extent of contraction is less. Also pre-culture time slows or prevents the self-sorting of two different cell types which enables control over the relative position of the cells in the macrotissue. While not wishing to be bound by theory, it is believed these results indicate that during pre-culture the cells are maturing their cell to cell contacts and also making extracellular matrix proteins, all of which are affixing or "gluing" the cells together in their respective positions and making them less reactive when it comes to fusing with other cells or other microtissues. This overcomes a problem with monodispersed cells, which is that they are too reactive, fuse with neighboring cells too quickly and self-sort too extensively. By using pre-culture time, building blocks of prescribed size and cell types can be employed. These building blocks can then be fused so that they retain the desired structure and form "proto-tissues" which can be employed in tissue regeneration and organ replacement.

Preferably, the microtissues to be seeded into the mold are spheroidal or toroidal in shape, although microtissues of any shape (for example, honeycomb) may be employed. A minimum of two microtissues must contact one another in order to assay fusion, the maximum number of microtissues may vary with the size of the microtissues to be tested and the size and shape of the micromold in which they are to be tested. With respect to fusions of spheroidal microtissues, spheroids of between two cells and three thousand cells are preferred because, as is known in the art, at very high cell numbers spheroids are limited by diffusion capacity. Although the fusion of spheroids is the simplest geometry to study the fusion process, the lessons learned about fusion of spheroids are applicable to the fusion of larger, more complex structures. Controlling fusion of spheroids and larger structures are anticipated to be useful for tissue engineering and other applications such as three-dimensional in vitro models for drug discovery. Microtissues that are in non-spheroidal shapes, for example, toroids and honeycombs, can be virtually unlimited in size and cell number because such structures contain lumen to permit the diffusion of molecules and nutrients and the like.

Honeycombs have the advantage for generating a relatively large structure with lumens that permit transport of nutrients and the like so cells remain viable. Honeycombs can be stacked to form units of yet increased size that continue to permit transport of nutrients and the like.

Spheroids of about 100 μm to about 300 μm are described herein.

The microtissues employed in this method can be produced using any of the known methods of producing microtissues: hanging drop, spinner culture or the method disclosed in PCT Patent Publication No. WO 2007/087402 published 2 Aug. 2007 (Application No. PCT/US2007/002050 filed 24 Jan. 2007). The microtissues can be a single cell type or they can be two or more different cell types that have been aggregated. The two or more different cell types may or may not have self-sorted into specific positions within the microtissue. A microtissue of one cell type may be combined with a microtissue composed of more than one cell type. In addition, the microtissues can be simple spheroids in shape or they can be more complex in shape, such as a toroid or a honeycomb. Differently shaped microtissues may be combined (for example spheroid with toroid). Microtissues of different sizes may be employed. The nonadhesive substrate into which the at least two microtissues are placed so as to effect contact with one another may be a trough in which adjacent microtissues contact each other at one point. Alternatively the nonadhesive substrate can be a three-dimensional substrate in which the microtissues can make single and/or multiple contacts with adjacent microtissues in all possible x, y and z dimensions. The critical parameter is the nonadhesive aspect of the substrate, which is necessary in order to allow tissue fusion to predominate over tissue spread on the substrate. Consequently, the substrate may be nonadhesive in the area in which tissue fusion is desired, and adhesive in other areas or portions in order to assist in guiding or directing the fusion process.

Example 1

Design, Fabrication and Casting of Micro-Molded Agarose Gels

Micro-molds were designed, fabricated, and cast as described in Napolitano et al., *Scaffold-free three-dimensional cell culture utilizing micromolded nonadhesive hydrogels, Biotechniques.* 43: 494, 496-500 (2007) and in PCT Patent Publication No. WO 2007/087402. Briefly, molds were designed using computer-assisted design (CAD) (Solid Works Corporation—Concord, Mass.). Wax molds from the CAD files were produced with a ThermoJet® rapid prototyping machine (three-dimensional Systems Corporation—Valencia, Calif.) and replicated in polydimethyl siloxane (PDMS) (Dow Corning—Midland, Mich.). Agarose gels were cast from the PDMS molds. Powder Ultrapure© Agarose (Invitrogen—Carlsbad, Calif.) was sterilized by autoclaving, and dissolved via heating in sterile water to 2% (weight/volume). Molten agarose (2.75 ml/mold) was pipetted into each PDMS mold and air bubbles were removed via pipette suction or agitation with a sterile spatula. After setting, gels were separated from the mold using a spatula, transferred to six-well tissue culture plates, and equilibrated overnight with tissue culture medium.

Using separate PDMS molds, recesses with different geometries were micro-molded into the surface of the agarose gels to create spherical, trough, toroid, or honeycomb shaped microtissues. Each micro-molded agarose gel was designed to fit within a well of a six-well plate. Spherical recesses were either 400 or 800 µm in diameter and contained 822 or 330 recesses/gel, respectively. Trough recesses were 2200 µm in length, 400 µm in width and there were 132 features/gel. Torioidal recesses were 1400 µm in diameter, with a circular trough 400 µm in width surrounding an agarose peg 600 µm in diameter and there were 64 features/gel. Honeycomb recesses were a lattice of seven contiguous tori and there were 18 features/gel. The width of the recess was 400 µm at all points and pegs within the honeycomb recess were 600 µm in diameter.

Example 2

Cell Culture and Isolation

Normal human fibroblasts (NHFs) derived from neonatal foreskins, and H35 rat hepatoma cells (H35s) were grown in Dulbecco's Modified Eagle Medium (DMEM) (Invitrogen—Carlsbad, Calif.) supplemented with 10% fetal bovine serum (FBS) (Thermo Fisher Scientific—Waltham, Mass.) and 1% penicillin/streptomycin (Sigma—St. Louis, Mo.). NHFs were maintained in a 37° C., 10% $CO_2$ atmosphere and H35s were maintained in a 37° C., 5% $CO_2$ atmosphere. Cells were trypsinized, counted and re-suspended to the desired cell density. The mono-dispersed cell suspension (200 µL) was then pippetted into the rectangular recess of each gel. Medium (3 mL) was added to the gel after approximately 20 minutes and was exchanged every other day.

Example 3

Assembly of Rod-Like Structures Using Spheroids as Building Units

Spheroids were generated using the micro-molded non-adhesive hydrogels made as described in Example 1. NHFs were seeded at a concentration of either $0.35 \times 10^6$ cells/822-well hydrogel or $1.0 \times 10^6$ cells/300-well hydrogel. Fourteen and five hydrogels, respectively, were seeded at these concentrations, resulting in microtissues of approximately 100 µm or 300 µm in diameter. The NHFs were cultured for one, four, or seven days within the hydrogels. Gels were inverted and centrifuged briefly at 800 rpm to retrieve the spheroid microtissues formed. The microtissues were resuspended in 200 µL medium and seeded onto a second micro-molded agarose gel with trough recesses and allowed to fuse for 24 hours. A corresponding control trough gel was seeded with mono-dispersed cells, $3 \times 10^6$ cells. This seeding number was chosen to match the number of cells in each recess across experimental groups given the efficiency of spheroid transfer.

The results are shown in FIGS. 1A-1F. Rod length is plotted as a function of fusion time. The microtissues cultured for one day are indicated by the open circles, for four days are indicated by the closed triangles, and for seven days are indicated by the open triangles. Representative images of the initial and final time point are shown for mono-dispersed cells (FIGS. 1A and 1B), one day (FIGS. 1C and 1D), four day (FIGS. 1E and 1F) and seven day pre-cultured microtissues (FIGS. 1G and 1H). Scale bars are 200 µm. This experiment demonstrates that the kinetics of microtissue assembly and steady-state length can be controlled by varying pre-culture time of large microtissue building units.

To determine if spheroids could be fused to form larger, more complex microtissues, we harvested and seeded NHF spheroids into micro-molds with toroidal or honeycombs features made as previously described in Example 1. NHFs were seeded at a concentration of $2.7 \times 10^6$ cells/822-well hydrogel, resulting in microtissues approximately 300 µm in diameter which were seeded into the micro-molds with toroidal or honeycomb features. The results are shown in FIGS. 6A-6D. The spheroids settled into the recesses, contacted one another, and fused over a 24 hour period to form a toroidal or honeycomb shaped microtissue. The resulting microtissues displayed smooth edges and appeared similar to those assembled from mono-dispersed cells in terms of shape, size and stability.

Example 4

Kinetics and Extent of Fusion in Rod-Like, Toroid and Honeycomb Structures Using Spheroids as Building Units The kinetics and extent of tissue fusion in the resulting rod structures of Example 3 was monitored by time lapse microscopy and rod contraction measured over 24 hours. Images of approximately 20 rods were captured every 20 minutes for 24 hours. Toroid and honeycomb shapes from Example 3 were imaged immediately after seeding and after 24 hours. Temperature and $CO_2$ percentage within the chamber were regulated by an incubator XL-S1-$CO_2$-control module (Pecon GmbH—Erbach, Germany). Rod microtissue length was measured using ImageJ (National Institute of Health, Bethesda, Md.) using the count particles function. The length of the rod structure was approximated by the major axis of a fitted ellipse. Recesses with too many spheroids or incompletely filled recesses were omitted from the analysis. The results are shown in FIGS. 1A-1F. Representative images of the initial conditions when the spheroids or mono-dispersed were first seeded (FIGS. 1A, 1C, 1E, 1G) and their final rod conformation after 24 hours (FIGS. 1B, 1D, 1F, 1H) are also shown. In all cases, the initially measured rod length was equal to the length of the trough recess, approximately 2.2 mm. Rod microtissues formed by mono-dispersed NHFs decreased in length exponentially in the first 600 minutes of assembly, then gradually approached their final length which approximated a spheroid. When NHF spheroids were pre-cultured for one day prior to fusion, similar exponential kinetics of rod contraction was also observed. However, the initial decline in length was not as rapid and the length of the assembled rod was significantly longer at 24 hours. When spheroids were pre-cultured for four or seven days prior to fusion, rod contraction was slowed considerably, proceeded with linear kinetics and rods after 24 hours were longer.

Figure 5:
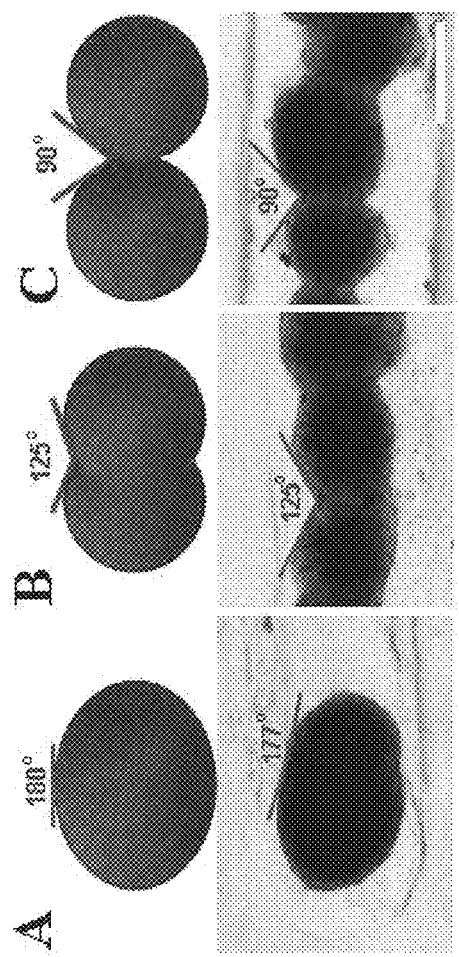
FIGS. 5A-5C: The extent of microtissue fusion is less complete with increasing pre-culture time. The average angle between fused spheroids within rod microtissues was measured as shown (A-C), with a 180° angle indicating a microtissue with no obvious fusion point. Error bars in results are standard deviation. Scale bar is 200 μm.
Figure 5:
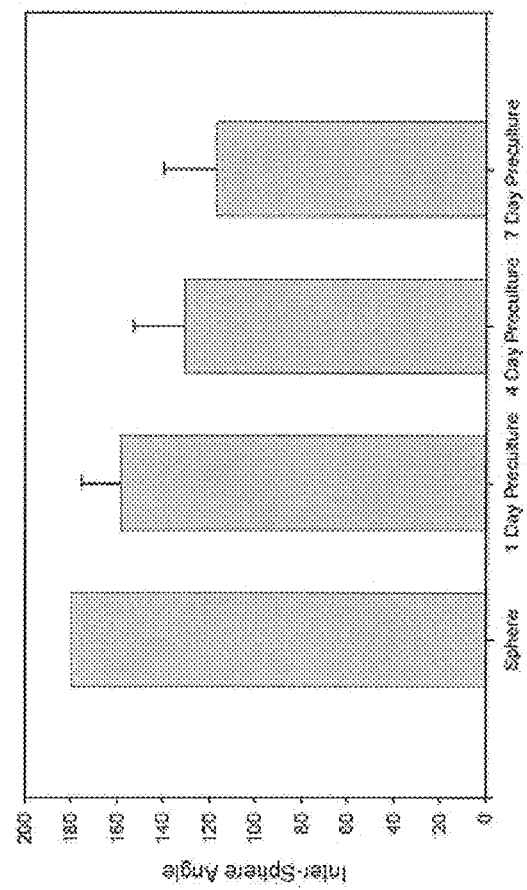
Figure 6:
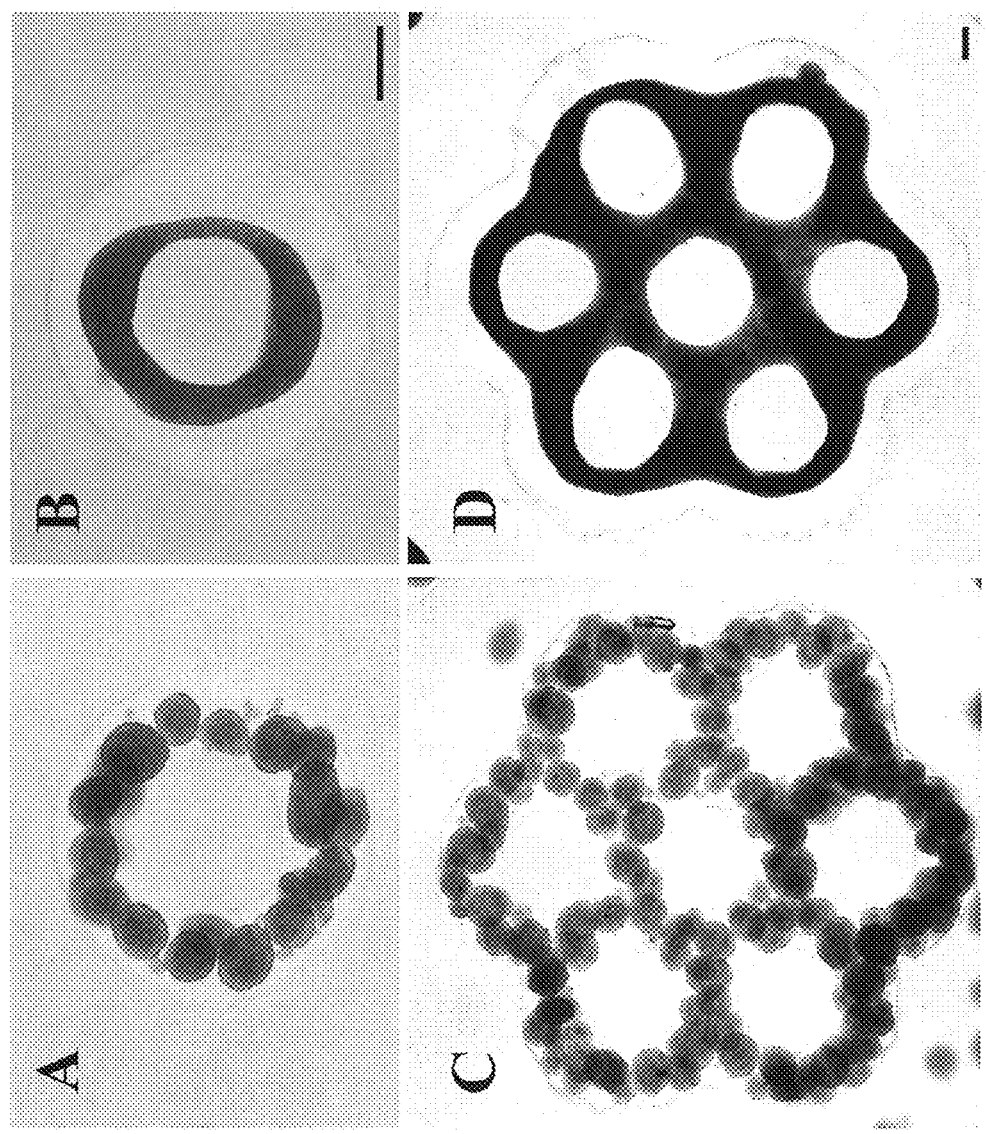
FIGS. 6A-6D: Complex shapes can be assembled using spheroids as building units. NHF spheroids were generated, then harvested and seeded into molds with toxoid (A, B) and honeycomb (C, D) features. Representative images of fusion are shown at the initial time point (A, C) and at a steady-state time point 24 hours after assembly (B, D). Scale bar is 200 μm.

Fusion angle within microtissues was measured between adjacent spheroids with an obvious acute angle. Adjacent spheroids with an unclear or obtuse fusion angle were omitted from the analysis. An angle of 180 degrees suggested a perfectly smooth transition between building units. The results are shown in FIGS. 5A-5C. The fusion angle of rod microtissues formed from large spheroids was the most reliable to measure because they were arranged in a more linear configuration and each spheroid usually contacted only two adjacent spheroids, whereas smaller spheroids typically contacted greater than two adjacent spheroids. For large spheroids, the fusion angle of adjacent spheroids decreased with pre-culture time with 7 day spheroids having the smallest angle. This data is consistent with the rod length measurements and suggests that increasing pre-culture time decreases fusion. Spheroids pre-cultured for one day formed smooth seamless ellipsoids, whereas seven-day pre-cultured spheroids formed structures where fusion was reduced and each of the connected spheroids were still discernible.

Example 5

SEM Examination of Fusion Process

Figure 4:
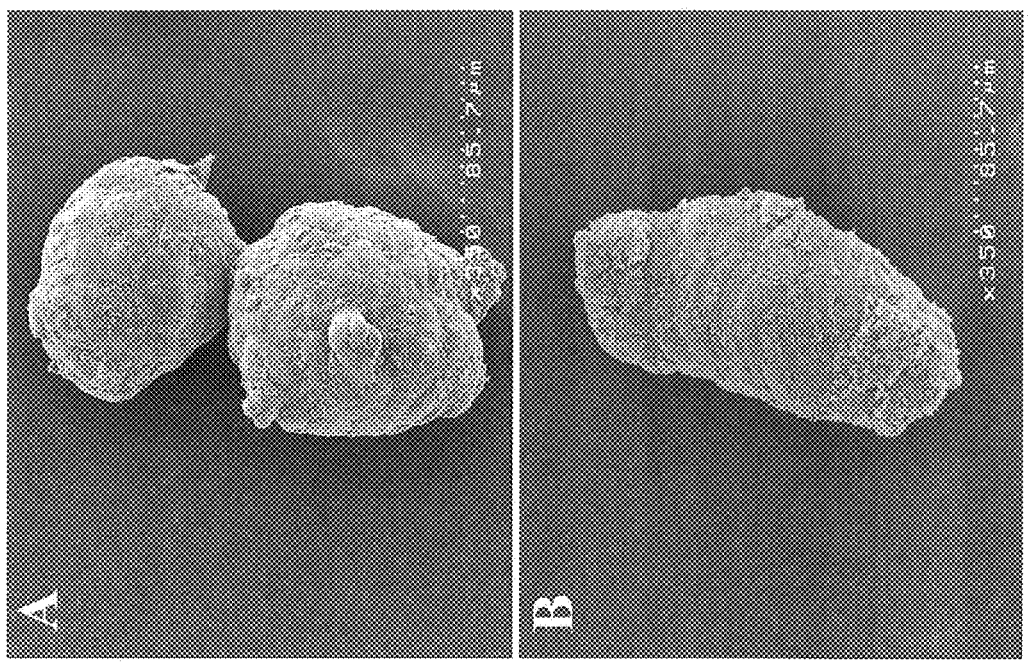
FIGS. 4A and 4B: Scanning electron micrographs of NHF microtissue fusion. Microtissues were pre-cultured for one day, allowed to fuse in trough recesses, then fixed approximately three (A) and 24 (B) hours after initial fusion. Microtissues were connected by a small bridge at three hours and formed a coherent microtissue after 24 hours.

The spheroid fusion process was examined using scanning electron microscopy was observed with a Hitachi S-2700 Scanning Electron Microscope (SEM; Hitachi—Toyko, Japan) using an acceleration current of 8 kV. Microtissues were fixed in Karnofsky's solution (2% paraformaldehyde and 2% gluteraldehyde in PBS) for at least one hour. Samples were dried using a critical point drier (Ladd Research—Wilmington, Vt.) and added to a stub using double-sided carbon tape. Samples were sputter coated (Emitech K550—Houston, Tex.) with gold-palladium for 4 minutes at 20 mA. Large diameter NHF spheroids were cultured for one day, then combined in a micro-mold with trough features and fixed at three and 24 hours. The results are shown in FIGS. 4A and 4B. Cell morphology and spheroid surface morphology did not appear to change at the point of fusion. After 24 hours of fusion, the resulting microtissue was a single structure with no distinguishable seams between spheroid building units.

To be sure fused microtissues were viable, rods assembled from 7 day pre-cultured spheroids were stained with the LIVE/DEAD stain. Viability of fused microtissues was assessed with the LIVE/DEAD® Viability/Cytotoxicity Kit (Invitrogen). Medium was removed, hydrogels were rinsed once with 3 ml of phosphate buffered saline (PBS) (Sigma), and 300 µl of PBS containing 2 µM calcein-AM and 4 µM ethidium homodimer (LIVE/DEAD® Viability/Cytotoxicity Kit) (Invitrogen—Carlsbad, Calif.) was added to the seeding chamber. Plates were protected from light and incubated at room temperature for 30 minutes, then observed using wide field fluorescent microscopy. The results are shown in FIGS. 1A-6D. Almost all cells were viable as indicated by the strong calcein-AM signal. Several dead cells were observed in small aggregates throughout the microtissue as shown by a few bright red dots.

Example 6

Effect of Maturity and Size on Fusion

To determine the effect of microtissue maturity on fusion, mono-dispersed NHFs were seeded into a gel with circular features to form spheroids approximately 300 µm in diameter. These spheroids were cultured for one, four, or seven days before they were harvested and seeded into the agarose mold containing trough features. For comparison, a separate gel was seeded with mono-dispersed NHFs and rod contraction over time was measured. The results are shown in FIGS. 1A-1F.

To determine the effects of microtissue size on fusion, mono-dispersed NHFs were seeded into a gel with circular features to form smaller spheroids (100 µm diameter). These spheroids were cultured for one, four, or seven days before they were harvested and tested in the fusion assay, all as described in Example 3. The results are shown in FIGS. 2A-2E. Representative images of the initial conditions (FIGS. 2A, 2C, 2E, 2G) and their final rod conformation after 24 hours (FIGS. 2B, 2D, 2F, 2H) are also shown When small NHF spheroids were pre-cultured for one day, fusion, as measured by rod contraction, proceeded at an exponential rate but slower than mono-dispersed cells. When small spheroids were pre-cultured for four or seven days, fusion was again slowed considerably, proceeded with linear kinetics with day seven spheroids having the slowest rate of rod contraction.

Example 7

Effect of Maturity and Size on Rod Length

Figure 3:
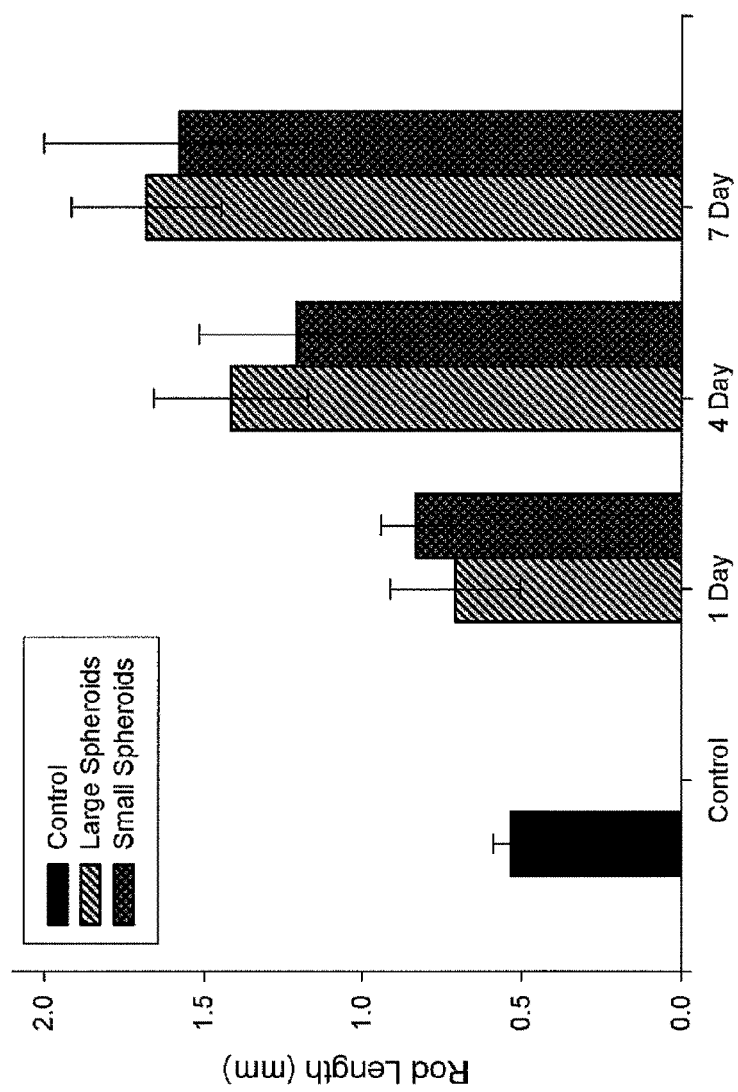
FIG. 3: Steady-state microtissue length is independent of building unit surface area after one, four, or seven days of building unit pre-culture time. Steady-state rod length after 24 hours of fusion in a trough mold is presented as a function of microtissue pre-culture time for mono-dispersed cells (black), large spheroids (diagonal lines), and small spheroids (cross-hatch) building units. Error bars are standard deviation.

To determine if microtissue maturity or microtissue size resulted in significant differences in rod length, rods were measured after twenty four hours and statistical comparisons made. The results are shown in FIG. 3. The most significant differences occurred due to microtissue maturity. Rod length for the mono-dispersed cell control was 0.51±0.08 mm. One day of spheroid pre-culture resulted in rods 0.81±0.12 mm for small spheroid building units and 0.73±0.15 mm for large spheroid building units. Four days of spheroid pre-culture resulted in rods of 1.21±0.31 mm for small spheroid building units and 1.42±0.24 mm for large spheroid building units. Seven days of spheroid pre-culture resulted in rods of 1.58±0.43 mm for small spheroid building units and 1.68±0.24 mm for large spheroid building units. The differences between mono-dispersed cells, 1 day pre-culture, 4 day pre-culture, and 7 day pre-culture groups were all statistically significant for both small and large spheroids. However, none of the differences between small and large spheroids were statistically significant (students t test, $p=0.05$).

Example 8

Characterization of NHF-H35 Cell Sorting in Tissue Fusion

Figure 8:
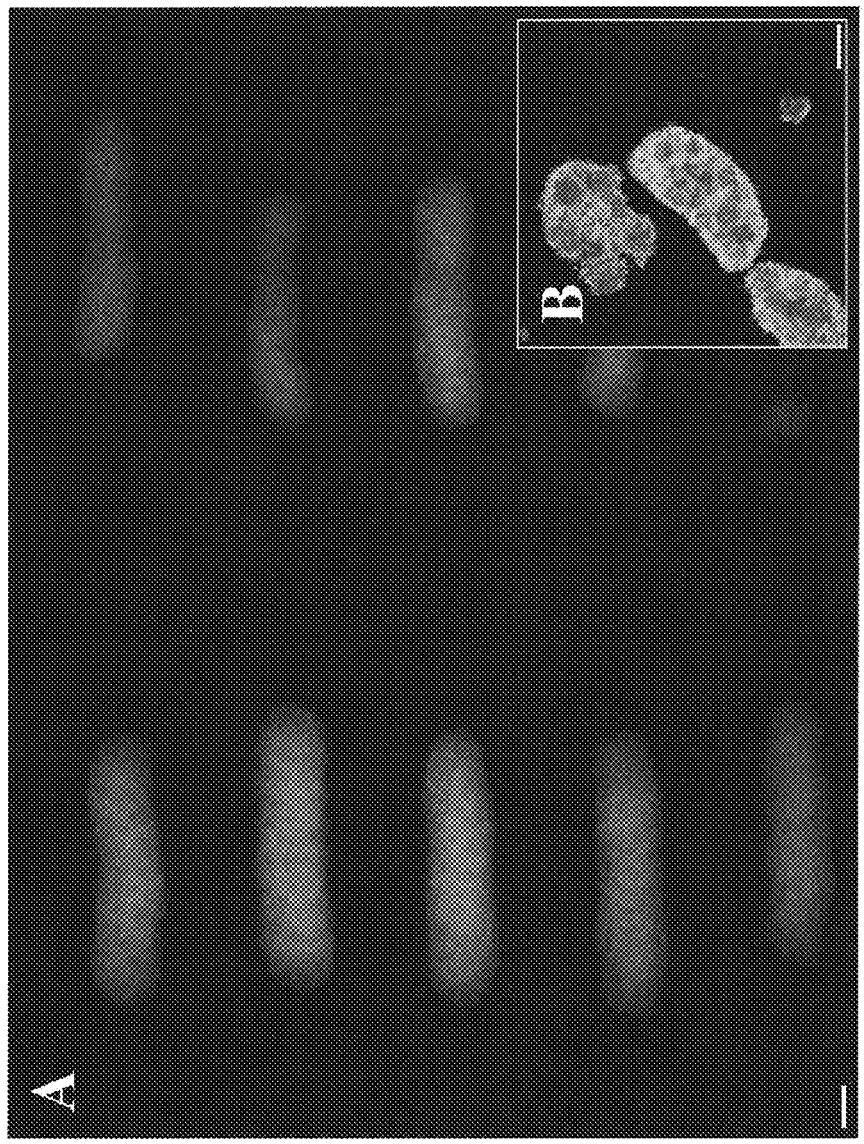
FIGS. 8A and 8B: Sorting can be further controlled by pre-culturing heterotypic building units. NHFs and H35s were fluorescently labeled with cell tracker red and green, respectively, then seeded in co-culture. After 24 hours of assembly, the two-layer spheroids were harvested and seeded within a mold with trough recesses. (A) After 24 hours, NHFs were coated by a thin layer of H35s, and these building units were tightly packed within the shape. (B) Inset: A confocal overlay of the same shape. Scale bar is 200 μm.

To determine if spheroids formed by a mix of two cell types could serve as building units, NHFs and H35s were fluorescently labeled with cell tracker red and green, respectively, then seeded and allowed to form heterotypic spheroids for 24 hours as described in previous examples. Cell tracker red (CMPTX; Invitrogen) was prepared by dissolving 50 µg of the stain in 7.1 µL of dimethyl sulfoxide (DMSO; Acros—Geel, Belgium) and 14.1 mL of serum-free DMEM. Cell tracker green (5-chloromethylfluorescein diacetate, CMFDA; Invitrogen) was prepared by dissolving 50 µg of the stain in 10.8 µL DMSO and 10.8 mL serum-free DMEM. NHFs were stained with cell tracker red and H35s were stained with cell tracker green. Cells were incubated in these solutions for 45 minutes at 37° C. Labeled cells were harvested by trypsinization, mixed (1:1) and then seeded into micro-molded agarose gels to form heterotypic spheroids. In each spheroid that formed, the NHF core was surrounded by an outer H35 coating. These building units were harvested and allowed to fuse in a micro-mold containing trough recesses. The results are shown in FIGS. 8A and 8B. In the resulting rod structure, small distinct NHF spheroids were tightly packed throughout the structure, each coated by a thin layer of H35s (see FIG. 8A). The inset (FIG. 8B) shows a confocal overlay of the same shape.

Example 9

Sorting Behavior can be Controlled by Pre-Culture Time of Building Units

To determine if microtissue pre-culture could be used to control the relative positions of two different cell types in a complex, heterotypic microtissue, mixtures of HNFs and H35s were examined. Pair-wise combinations (experimental matrix of 3×3 equal to a total of 9 combinations) of monodispersed cells or spheroids pre-cultured for different days were made. The experimental groups of the matrix were H35 (mono-dispersed cells, spheroids pre-cultured 1 day and spheroids pre-cultured 4 days) and NHF (mono-dispersed cells, spheroids pre-cultured 1 day and spheroids pre-cultured 4 days). Combinations were simultaneously seeded into micro-molded agarose gels containing trough recesses and allowed to fuse for 24 hours before observation with wide field fluorescent microscopy, as described in Example 3. The results are shown in FIGS. 7A-7I.

Figure 7:
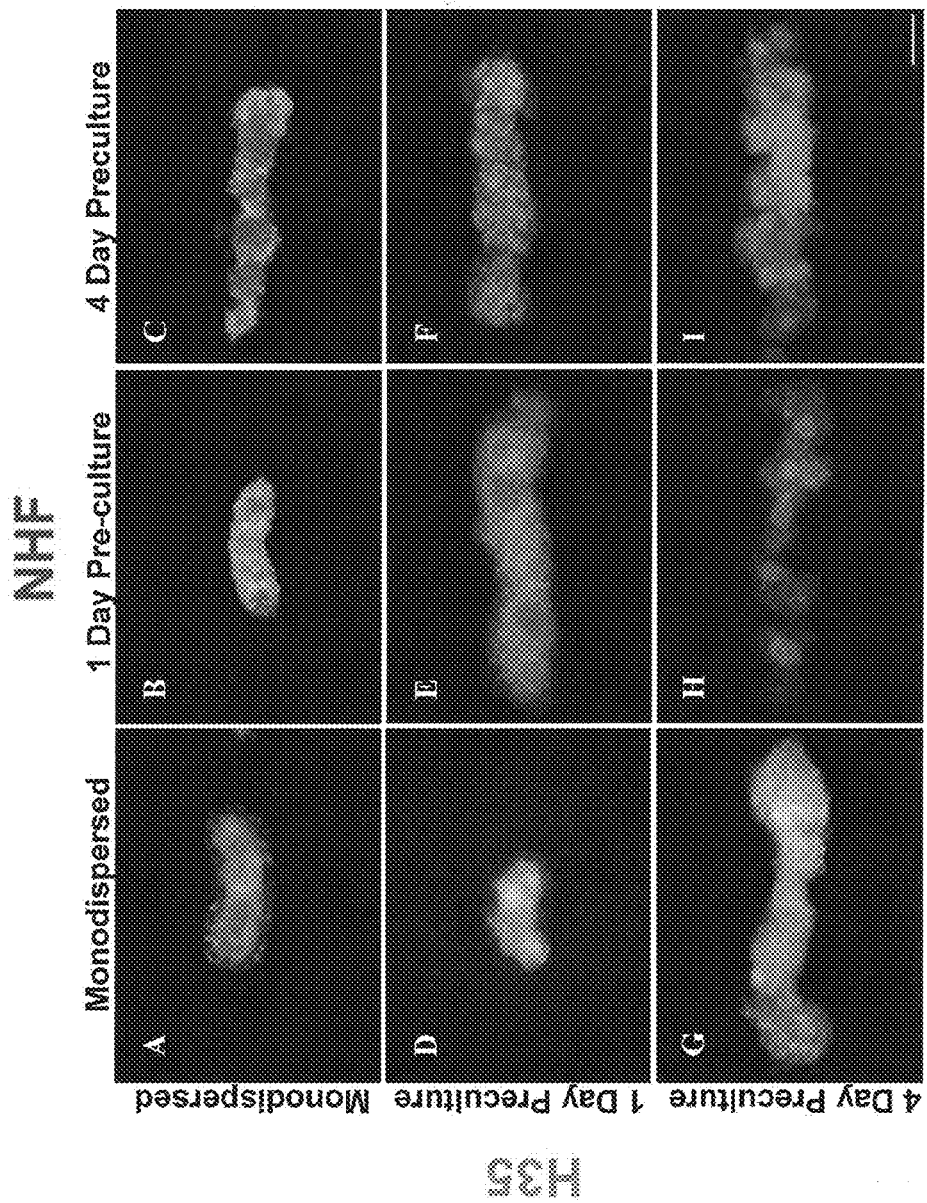
FIGS. 7A-7I: The sorting behavior of NHFs and H35s in mixed microtissues can be controlled based on pre-culture time of building units. Columns represent NHFs as mono-dispersed cells (A, D, G) spheroids pre-cultured for one day (B, E, H), and four days (C, F, I) labeled with cell tracker red. Rows represent H35s as mono-dispersed cells (A, B, C), spheroids pre-cultured for one day (D, E, F), and four days (G, H, I) labeled with cell tracker green. Scale bar, 200 μm.

When mono-dispersed NHFs and mono-dispersed H35s were mixed, they formed a microtissue and self-sorted to have a single NHF core and a contiguous H35 outer coating (FIG. 7A). This same pattern of a single NHF core and contiguous H35 outer coating was also evident when mono-dispersed NHFs were mixed with H35 spheroids pre-cultured for one day (FIG. 7D). In microtissues formed by mono-dispersed NHFs mixed with H35 spheroids pre-cultured for four days, the NHFs formed multiple spheroids some of which were not entirely covered with an H35 outer coating and large clusters of H35s were also evident in the central region (FIG. 7G). Mono-dispersed NHFs did not exclusively occupy the central region of the microtissue when mixed with four day H35 spheroids. In certain areas of the microtissue, this created an "inside out" structure with an H35 core and an NHF coating in certain samples. When mono-dispersed H35s were mixed with NHF spheroids pre-cultured for one or four days, the microtissues that formed had a near contiguous outer coating of H35s and multiple NHFs spheroids some that were fused with one another and others that were entirely surrounded by H35s (FIGS. 7B and 7C). A similar general pattern was seen in the four remaining mixes; H35 one day spheroids with either NHF one or four day spheroids (FIGS. 7E and 7F), and H35 four day spheroids with NHF one or four day spheroids (FIG. 7H, I). Some differences were also evident. Larger exclusively H35 areas were observed with increased pre-culture time of H35 spheroids (FIGS. 7E-7I). Longer pre-culture times of spheroids of both cell types resulted in less cell sorting and cell mixing. The pre-cultured spheroids were more stable and appeared to fuse in place. Our observations suggest that these structures had reached steady-state after 24 hours of fusion and similar organization was observed after four days of culture.

Example 10

Fusion of Toroidal Shaped Microtissues

To determine if microtissues in the shape of toroids could be fused, we seeded H35 cells into micro-molded agarose gels and self-assembled toroidal shaped microtissues as in Example 3. Forty-eight hours after formation, toroidal shaped microtissues were harvested from the micro-molds and tested for fusion. To determine if the outer circumference of toroids was capable of undergoing fusion, two toroids were placed apposed on flat agarose. The results are shown in FIGS. 10A-10J. After making contact, the toroids fused, forming a double-lumen structure. Similar to the behavior of individual units, toroid and lumen diameters decreased, and toroid width increased over time. Additionally, cell density, which was initially uniform, became denser toward the lumen for both units. However, at the junction of the two units, the areas of high cell density fused to form a continuous internal figure eight structure of high cell density.

To determine if toroids could be fused on their top and bottom surfaces, a second micro-mold was used to guide fusion. Forty-eight hours after formation, toroids were harvested and transferred to a second micro-mold containing toroidal shaped recesses, but with a nonadhesive conical-shaped peg, in which another toroid has also self-assembled for 48 hours. Toroids from the first micro-mold were carefully stacked on the second toroid and side view brightfield images were taken to observe fusion. The results are shown in FIGS. 10A-10J. Over time, the toroids fused on their top and bottom surfaces.

Example 11

Fusion of Toroidal Shaped Microtissues into a Large, Multi-Torus Structure

To determine if toroids could be fused to form a larger structure, 1135 cells were seeded into micro-molded agarose gels and self-assembled toroidal shaped microtissues as in Example 3. Forty-eight hours after formation, toroidal shaped microtissues were harvested from the micro-molds (micro-molds containing 81 toroids each). The toroids were combined and added to a single, large well cast in nonadhesive agarose. The results are shown in FIGS. 11A-11F. The toroids settled and formed a multi-layered pile of toroids at the bottom of the well. Settling was not entirely random, with most toroids lying flat with their lumens oriented along the z axis. Over time, the toroidal shaped microtissues fused and formed a large, multi-torus structure. Seven days later, in wells that were not perfused, the toroids and a control of spheroids (about 200 µm, micromolds containing 822 spheroids each), were stained for viable cells. Seeding density was kept uniform for toroid and spheroid gels, with a total seeding density of $2 \times 10^6$ cells/gel, with comparable yields upon harvesting. Compared to the spheroids, the toroids showed evidence of more luminal space and increased cell viability.

Example 12

Self-Assembly and Tissue Fusion of Toroid-Shaped Minimal Building Units

Design, Fabrication and Casting of Micro-Molds

Micro-molds were fabricated as previously described (17). Briefly, micro-molds were designed using computer-assisted design (CAD) (Solid Works Corporation—Concord, Mass.). Wax prototypes from the CAD files were produced with a ThermoJet® rapid prototyping machine (three-dimensional Systems Corporation—Valencia, Calif.) and then replicated in polydimethylsiloxane (PDMS) (Dow Corning, Midland, Mich.).

Six different designs with toroidal-shaped recesses were fabricated to fit in a E-well plate. Four micro-molds were designed with peg diameters of about 400, about 600, about 800 or about 1000 µm, with circular track widths of about 400 µm and peg heights of about 800 µm, and about 100, about 81, about 64, or about 25 features/gel, respectively. Two micro-molds were designed with circular track widths of about 600 or about 800 µm, with peg diameters of about 600 µm and peg heights of about 800 and about 49 or about 36 features/gel, respectively.

Agarose gels were cast from PDMS micro-molds. Powder Ultrapure© Agarose (Invitrogen—Carlsbad, Calif.) was autoclaved and then dissolved via heating in sterile water to about 2% (weight/volume). About 2.75 mL of molten agarose was pipetted into each PDMS micro-mold and air bubbles were removed. After setting, gels were removed and transferred to six well plates where they were equilibrated with tissue culture medium (17, 18).

Side view polyacrylamide gels with a single row of 12 recesses were cast directly from the wax prototypes to allow observation in the vertical plane. To produce gels, 10 mL of about 35% prepolymer solution containing acrylamide-bis-acrylamide (29:1 mix ratio), Tris buffer (pH 6.8), and Dulbecco's modified Eagle's medium (DMEM) (Invitrogen) was degassed and polymerized by addition of 50 µl of 10% ammonium persulfate and 100 µl N,N,N,N-tetramethylethylenediamine Gels were equilibrated overnight, rinsed with 3 mL of medium, and stored in medium until use (17, 18).

Cell Culture, Toroid Assembly and Fusion

The rat hepatocyte cell line (H35) (18) was expanded in DMEM supplemented with 10% fetal bovine serum (FBS; Thermo Fisher Scientific—Waltham, Mass.) and 1% penicillin/streptomycin (Sigma—St. Louis, Mo.) and maintained at 37° C., 5% $CO_2$ (17-19). Cells were trypsinized, counted, and re-suspended in 200 µl and pippetted into the rectangular recess. An agarose gel with 81 features was seeded with $2\times10^6$ cells producing toroids with about 24,700 cells/toroid. For the polyacrylamide gels, 70 µl of cell suspension was used (about $3.0\times10^5$ cells) (about 24,700 cells/toroid). Gels were incubated for 20 minutes before 3 mL of medium was added. Medium was exchanged every other day (17, 18).

Toroids were self-assembled for 48 hours and then harvested by inverting the gels in a new dish with 3 mL of medium and gently centrifuged (700 rpm, 1 min). Harvested toroids were transferred to a 24-well plate whose wells were coated with agarose and monitored over a period of 10 days, with images captured daily. Toroid width and lumen diameter were measured using ImageJ (National Institutes of Health, Bethesda, Md.).

For stacking experiments, individual toroids were aspirated into a 1-mL micropipette and carefully transferred to a polyacrylamide gel already containing toroids that had self-assembled for 48 hours. This gel contained 12 toroidal shaped recesses (trough about 400 µm wide) with a cone-shaped peg (about 600 µm diameter, height about 600 µm and slope about 85°). With the aid of a dissecting microscope, toroids were carefully stacked on the toroid self-assembled around the conical peg. Gels were given fresh medium and returned to the incubator.

Large, multi-luminal structures were assembled by multi-dimensional fusion of numerous toroids. Toroids self-assembled for 48 hours were harvested and seeded into another agarose gel containing one large recess with a rounded bottom (about 6 mm diameter) that had been equilibrated in culture medium. Medium was exchanged every other day.

Microscopy

Bright-field, phase-contrast, and fluorescent images were obtained using a Carl Zeiss Axio Observer Z1 equipped with an AxioCam MRm camera (Carl Zeiss MicroImaging, Thornwood, N.Y.) and captured using Axiovision Software. Bright-field side-view images were captured using a Mitutoyo FS-110 microscope modified to lie horizontally, equipped with a Nikon CoolPix 990 digital camera. Side view fluorescent images were captured with the aid of a small mirror (Thorlabs, Newton, N.J.) placed adjacent to the gel.

For scanning electron micrographs (SEM), toroids were fixed in Karnofsky's solution (phosphate buffered saline (PBS) supplemented with 2% paraformaldehyde/2% glutaraldehyde). Samples were critical point dried (LADD Research, Williston Vt.) and sputter-coated with gold/palladium (Emitech, Sussex, United Kingdom) and imaged using a Hitachi S-2700 SEM (Tokyo, Japan).

Cell Tracker and Live/Dead Viability Fluorescent Staining

Cell position was assessed using Cell Tracker chloromethylfluorescein dyes (Invitrogen). Cell Tracker red (CMTPX) was prepared by dissolving 50 µg of the stain in 7.1 µl of dimethyl sufoxide (DMSO; Acros—Geel, Belgium) and 14.1 mL of serum free DMEM. Cell Tracker green (CMFDA) was prepared by dissolving 50 µg of the stain in 10.8 µl of DMSO and 10.8 mL of serum free DMEM. Cells on tissue culture plates were stained by incubation for 45 minutes at 37° C. Green and red dyes were observed at an excitation/detection of about 492/517 nm, and about 577/602 nm, respectively.

Cell viability was assessed with LIVE/DEAD® Viability/Cytotoxicity Kit (L3224, Invitrogen). Medium was removed, gels were rinsed twice with 3 mL of PBS, and 300 µl of PBS containing 2 µM calcein-AM and 4 µM ethidium homodimer was added to the seeding chamber. Plates were protected from light and incubated at room temperature for 45 minutes, then observed using wide field fluorescence microscopy.

Statistics

Measurements were performed in triplicate, with results presented as the mean of all triplicate means. Error bars represent standard deviation. Statistical significance was evaluated using a Student's t-test at a probability of $P=0.05$.

Results

To form toroidal shaped micro-tissues, mono-dispersed H35 cells were seeded onto the agarose gels where they self-assembled multi-cellular toroids. To determine if the diameter of the toroid and its lumen could be controlled by micro-mold design, we tested four different diameters of the peg (about 400, about 600, about 800, and about 1000 µm) (FIGS. 12A-12D). The width of the circular trough was kept constant (about 400 µm) and each gel was seeded with the same number of cells (about $2\times10^6$ cells). By 48 hours, the toroids had contracted around the agarose peg. Thus, the diameter of each toroid and its lumen were dependent on the diameter of the peg.

Figure 13:
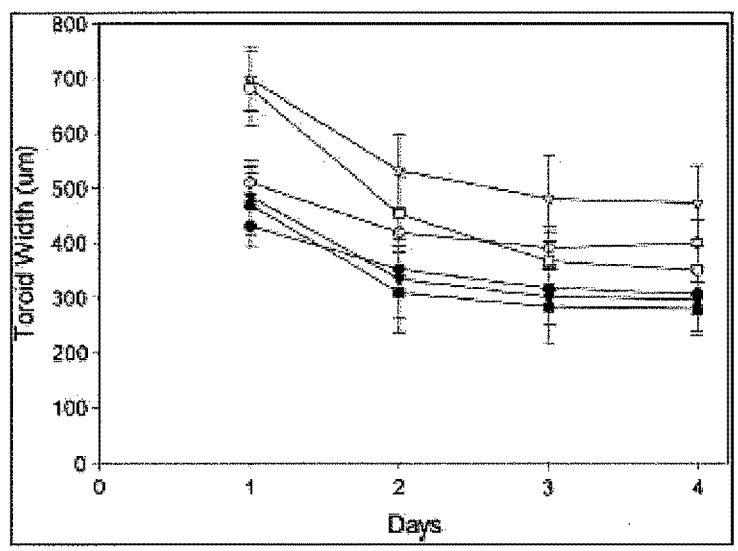
FIG. 13: Toroid width is independent of trough width. Mono-dispersed cells (about 20 [closed symbols] or about 40 [open symbols] cells/micron of circumference) were seeded onto micro-molds containing toroidal shaped recesses whose peg had the same diameter (about 600 μm) but whose circular tracks had varying widths of about 400 (●, ○), about 600 (▼, ∇), or about 800 (■, □) μm. Width of the toroids as a function of time is plotted for each design. n=39 (about 400 μm, about 20 cells/μm, ●), 47 (about 400 μm, about 40 cells/μm, ○), 45 (about 600 μm, about 20 cells/μm, ▼), 30 (about 600μm, about 40 cells/μm, ∇), 26 (about 800 μm, about 20 cells/μm, ■) and 11 (about 800 μm, about 40 cells/μm, □).

To determine if the toroid width could be controlled by the width of the circular track, we designed features whose pegs were the same (about 600 µm), but whose circular tracks varied in width (about 400, about 600, and about 800 µm) (FIG. 13). Each gel had different numbers of toroidal recesses, with cell seeding number normalized to two unique circumferences of the peg (about 20 or about 40 cells/micron of circumference). As the cells self-assembled, the widths (x-y) of the toroids decreased each day. At both seeding densities, toroid width was independent of the circular track width. Additionally, doubling the number of cells/gm of circumference did not double toroid width, suggesting that cells contribute to the z-thickness of the toroid as it self-assembles.

Figure 14:
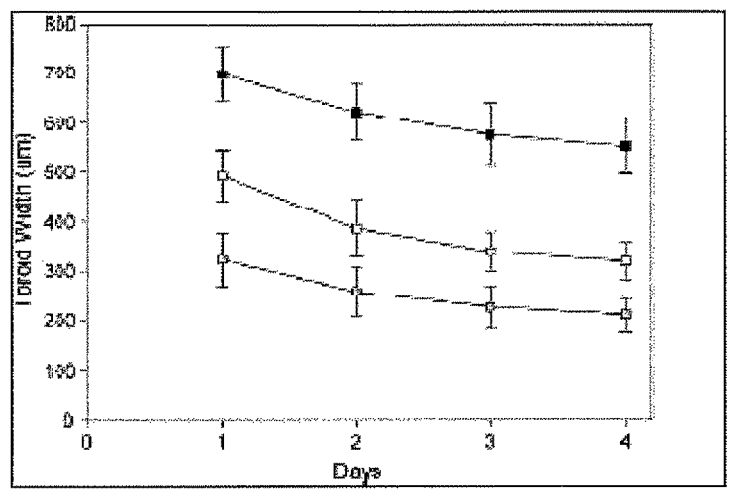
FIG. 14: Toroid width is dependent on the number of cells seeded into the micro-mold. Toroids were self-assembled from mono-dispersed cells seeded at 3 unique seeding densities of about 10 (▼), about 20 (□), and about 50 (▼) cells per micron of circumference, and observed daily for a period of 4 days.
Figures 15A, 15B, 15C, 15D, 15E, 15F, 15G, 15H:
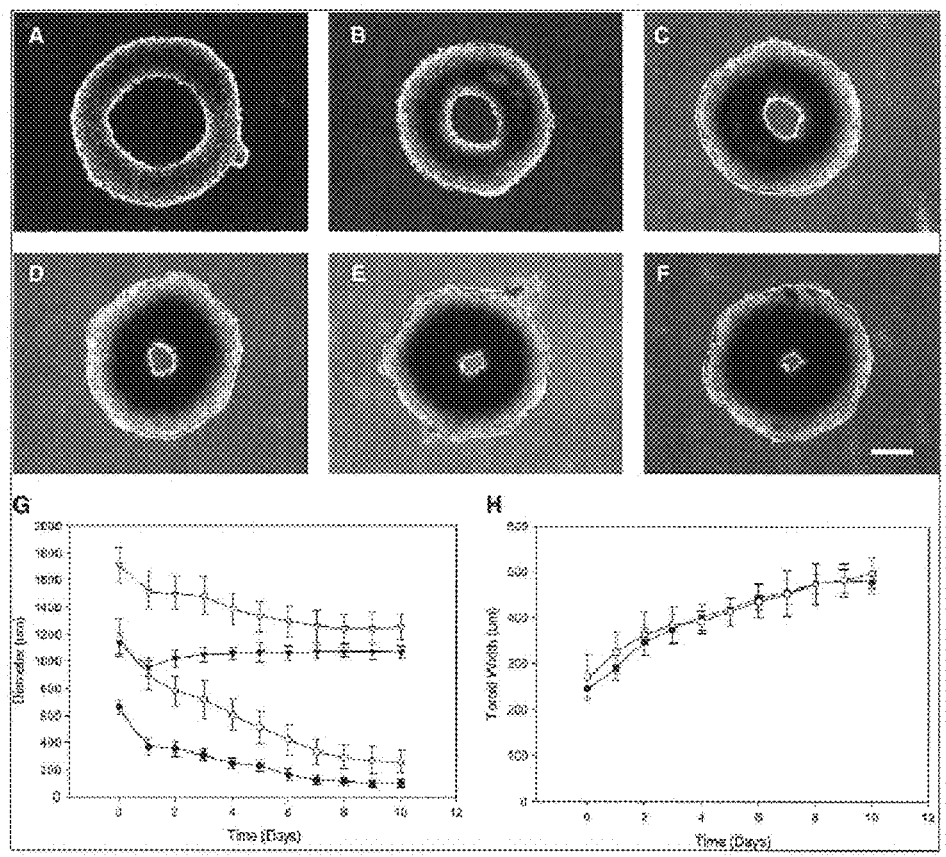
FIGS. 15A-15H: Toroids are stable building units, whose lumens narrow with predictable kinetics. Toroids were self-assembled and cultured for 48 hours prior to being harvested from the micro-molds. Toroids were placed on flat non-adherent agarose and observed over a period of 10 days. Representative bright-field images of toroids self-assembled in recesses with a about 600 μm peg diameter and about 400 μm circular track width are shown at days 0, 2, 4, 6, 8 and 10 (A-F). Lumen diameter (●, ○) and total diameter (▼, ∇) were measured as a function of time for toroids self-assembled in recesses with about 600 μm peg diameter (closed symbols) and in recesses with about 1000 μm peg diameter (open symbols) (G). Toroid width for the same samples (■, □) was also measured as a function of time (H). Scale bar is 200 μm.

To determine if the width of the toroids could be controlled by the cell seeding number, we picked one toroid design (trough width about 600 µm, peg diameter about 600 µm) and seeded it with varying numbers of cells (about 10, about 20 or about 50 cells/µm of circumference) (FIG. 14). As the cells self-assembled, the widths of the toroids decreased. When normalized, the widths of the toroids with about 10 and about 20 cells per micron of circumference had decreased about 35% by day 4, while the toroids with 50 cells per micron of circumference decreased only about 20%, suggesting that an upper threshold had been reached for efficient self-assembly.

To determine their stability, toroids were harvested and placed on flat agarose and allowed to contract over time. This was done for toroids assembled in micro-molds with about 600 µm peg diameter (about 600 µm toroid) or 1000 µm peg diameter (about 1000 µm toroid), both with about 400 µm circular track widths. The diameters of the toroid, its lumen, as well as the width of the toroid were measured over time (FIGS. 15A-15H). At 10 days, the outer diameter of about 600 µm toroid had decreased about 6% and its lumen diameter decreased about 85% with the largest decrease (about 44%) occurring in the first 24 hours after harvest. Thereafter, outer diameter decreased at a rate of approximately 1% per day and lumen diameter decreased at a rate of about 16% per day, until day 7, when the rate slowed. Likewise, the outer diameter of the about 1000 µm toroids decreased about 27% and the lumen diameter decreased about 77% by 10 days, with the largest decrease (about 24%) also occurring in the first 24 hours after harvesting. Thereafter, outer diameter decreased at a rate of about 2% per day and lumen diameter decreased at a rate of about 15%, per day, until day 7, when the rate slowed.

In contrast, the widths of both the 600 µm and 1000 µm toroids increased. After ten days, the widths of the 600 µm and 1000 µm toroids had increased about 95% and about 83%, respectively. The width of the 600 µm and 1000 µm toroids increased at rates of about 7.1% and about 6.4% per day, respectively. Despite their different starting diameters and different cell densities along their circumferences (about 600 µm, about 1000 µm toroids; about 13, about 25 cells/µm of circumference, respectively), the widths of the 600 µm and 1000 µm toroids increased with similar kinetics. In addition to increases in width, the 600 µm and 1000 µm toroids also increased in thickness (z dimension). This was evident from the bright field images which showed a decrease in transparency due to an increase in cell density. Increased cell density was not uniformly distributed around the toroid and was found closer to the lumen rather than the outer rim.

To determine if the outer circumference of toroids was capable of undergoing fusion, two toroids were placed apposed on flat agarose (FIGS. 10A-10J). After making contact, the toroids fused forming a double-lumen structure. Similar to the behavior of individual units, toroid and lumen diameters decreased, and toroid width increased over time. Additionally, cell density, which was initially uniform, became more dense toward the lumen for both units. However, at the junction of the two units, the areas of high cell density fused to form a continuous internal figure eight structure of high cell density.

Figures 16A, 16B:
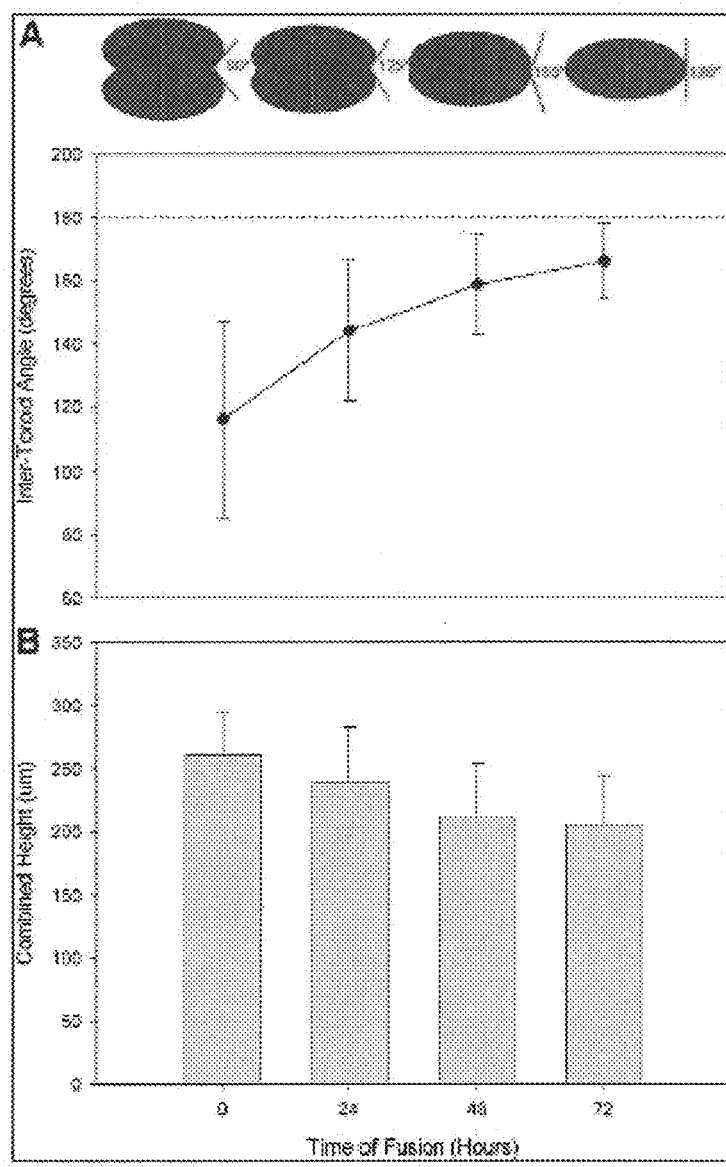
FIGS. 16A and 16B: Stacked toroids undergo fusion. From side-view bright-field images, the kinetics of fusion of stacked toroids was assessed by measuring the inter-toroid angle (diagram) (A). A reference line is shown at about 180°. The change in z thickness of the stacked toroids was also measured from the side-view images (B). Error bars represent standard deviation.
Figures 17A, 17B, 17C, 17D, 17E, 17F:
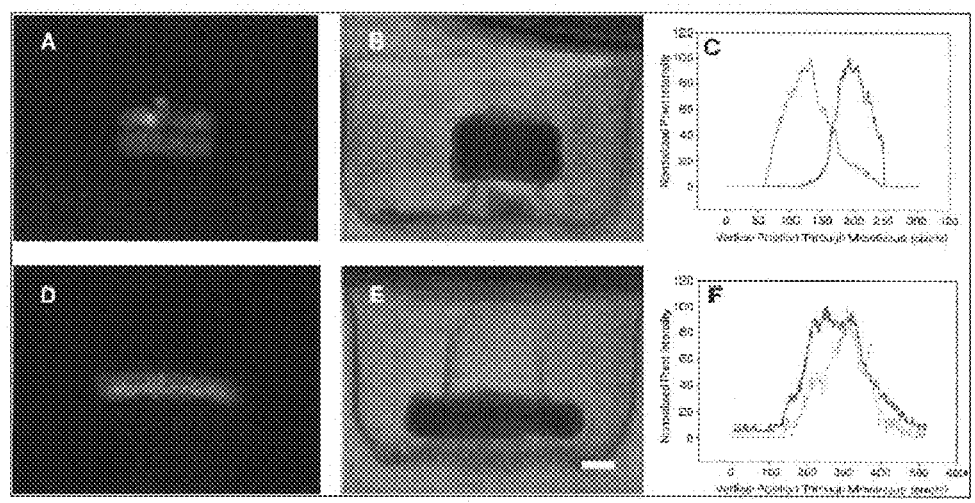
FIGS. 17A-17F: Toroids fuse and undergo minimal cell mixing. One fluorescently labeled red and one green toroid were cultured for 48 hours, stacked and fused for 48 hours. Fluorescent (A) and bright-field images (B) demonstrate fusion, but minimal cell mixing as confirmed by the fluorescence intensity profile (C). A control toroid (1:1 mix of monodispersed red and green cells) was cultured for 96 hours. Fluorescent (D) and bright-field images (E) demonstrate mixing of fluorescent signals as confirmed by the fluorescence intensity profile (F). Scale bar is 200 μm.
Figures 18A, 18B, 18C, 18D:
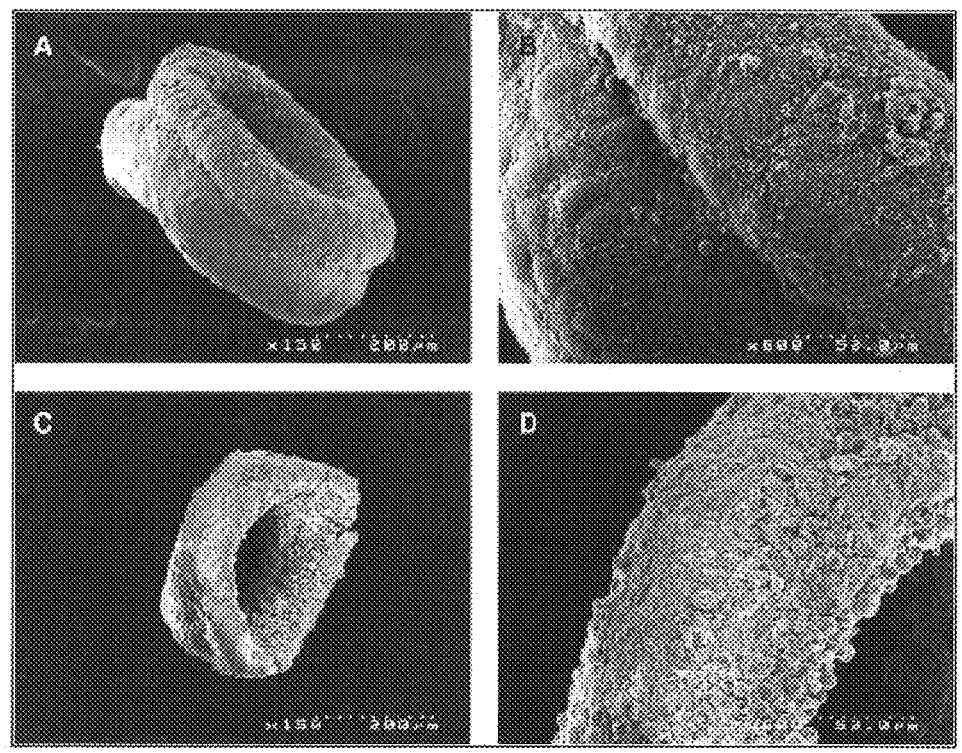
FIGS. 18A-18D: Scanning electron micrographs of toroid fusion. Toroids were cultured for 48 hours, and allowed to fuse around a peg, then fixed approximately 12 hours (A, B) and 72 hours (C, D) after initial fusion. An obvious furrow is observed throughout between initially distinct toroids after about 12 hours, and appears as a coherent tissue after about 72 hours.

To determine if toroids could be fused on their top and bottom surfaces, we used a second micro-mold to guide fusion. Toroids were harvested after 48 hours and transferred to a second micro-mold containing toroidal shaped recesses, but with a conical shaped peg, in which another toroid had also self-assembled for 48 hours. Toroids from the first micro-mold were carefully stacked on the second toroid and side view brightfield images taken to observe fusion (FIGS. 10A-10J). To quantify the kinetics of fusion, the inter-toroid angle was measured on each oblique side with an angle of 180° representing total fusion (FIGS. 16A and 16B). Variance in the inter-toroid angle was greatest at the start of the experiment due to the challenges of perfectly aligning the stacked toroids. As fusion progressed, the variance declined as the inter-toroid angle increased towards 180°. The combined z height or thickness of the stacked toroids was also measured. Thickness of the toroids harvested from the agarose micro-mold was about 113.6+/−21.2 and about 147.5+/−23.9 from the polyacrylamide micro-mold. After 72 hours, the thickness of two stacked toroids was about 205 µm, a decrease of about 21%. Thickness decreased 10% per day for the first 48 hours after which it remained stable.

To determine the extent of cell mixing between building units, the stacking assay was repeated using fluorescently labeled toroids (FIGS. 17A-17F). A red labeled toroid was stacked on a green labeled toroid and fluorescent side view images taken after 48 hours of fusion. The images and a representative vertical profile of fluorescence intensity indicated fusion, but minimal cell mixing between toroids.

SEM was used to visualize fusion of toroids (FIGS. 18A-18D). After 12 hours of fusion, the images show a fusion furrow at the junction of the two toroids. At 72 hours, a furrow can no longer be identified and the units have undergone a seamless fusion.

To determine if toroids could be used to form a larger structure, toroids (about 600 µm) were harvested (micromolds containing 81 toroids each) after 48 hours of self-assembly. The toroids were combined and added to a single large well cast in agarose (FIGS. 11A-11F). The toroids settled and formed a multi-layered pile of toroids at the bottom of the well. Settling was not entirely random, with most toroids lying flat with their lumens oriented along the z axis. Seven days later in wells that were not perfused, the toroids and a control of spheroids (about 200 µm, micromolds containing about 822 spheroids each), were stained for viable cells. Seeding density was kept uniform for toroid and spheroid gels, with a total seeding density of about $2\times10^6$ cells/gel, with comparable yields upon harvesting. Compared to the spheroids, the toroids showed more evidence of luminal space and increased cell viability.

REFERENCES

1. Griffith, C. K., Miller, C., Sainson, R. C., Calvert, J. W., Jeon, N. L., Hughes, C. C., and George, S. C. Diffusion limits of an in vitro thick prevascularized tissue. Tissue Eng 11, 257, 2005.
2. Khademhosseini, A., Langer, R., Borenstein, J., and Vacanti, J. P. Microscale technologies for tissue engineering and biology. Proc Natl Acad Sci USA 103, 2480, 2006.
3. Colton, C. K. Implantable biohybrid artificial organs. Cell Transplant 4, 415, 1995.
4. Carmeliet, P., and Jain, R. K. Angiogenesis in cancer and other diseases. Nature 407, 249, 2000.
5. Ko, H. C., Milthorpe, B. K., and McFarland, C. D. Engineering thick tissues—the vascularisation problem. Eur Cell Mater 14, 1, 2007.
6. Fidkowski, C., Kaazempur-Mofrad, M. A., Borenstein, J., Vacanti, J. P., Langer, R., and Wang, Y. Endothelialized microvasculature based on a biodegradable elastomer. Tissue Eng 11, 302, 2005.
7. McGuigan, A. P., and Sefton, M. V. Design criteria for a modular tissue-engineered construct. Tissue Eng 13, 1079, 2007.
8. McGuigan, A. P., and Sefton, M. V. Design and fabrication of sub-mm-sized modules containing encapsulated cells for modular tissue engineering. Tissue Eng 13, 1069, 2007.
9. McGuigan, A. P., and Sefton, M. V. The thrombogenicity of human umbilical vein endothelial cell seeded collagen modules. Biomaterials 29, 2453, 2008.
10. McGuigan, A. P., and Sefton, M. V. Vascularized organoid engineered by modular assembly enables blood perfusion. Proc Natl Acad Sci USA 103, 11461, 2006.
11. Boland, T., Mironov, V., Gutowska, A., Roth, E. A., and Markwald, R. R. Cell and organ printing 2: fusion of cell aggregates in three-dimensional gels. Anat Rec A Discov Mol Cell Evol Biol 272, 497, 2003.
12. Jakab, K., Neagu, A., Mironov, V., Markwald, R. R., and Forgacs, G. Engineering biological structures of prescribed shape using self-assembling multicellular systems. Proc Natl Acad Sci USA 101, 2864, 2004.

13. Mironov, V., Boland, T., Trusk, T., Forgacs, G., and Markwald, R. R. Organ printing: computer-aided jet-based three-dimensional tissue engineering. Trends Biotechnol 21, 157, 2003.
14. Mironov, V., Visconti, R. P., Kasyanov, V., Forgacs, G., Drake, C. J., and Markwald, A. R. Organ printing: Tissue spheroids as building blocks. Biomaterials, 2009.
15. Smith, C. M., Stone, A. L., Parkhill, R. L., Stewart, R. L., Simpkins, M. W., Kachurin, A. M., Warren, W. L., and Williams, S. K. Three-dimensional bioassembly tool for generating viable tissue-engineered constructs. Tissue Eng 10, 1566, 2004.
16. Wilson, W. C., Jr., and Boland, T. Cell and organ printing 1: protein and cell printers. Anat Rec A Discov Mol Cell Evol Biol 272, 491, 2003.
17. Napolitano, A. P., Chai, P., Dean, D. M., and Morgan, J. R. Dynamics of the self-assembly of complex cellular aggregates on micromolded nonadhesive hydrogels. Tissue Eng 13, 2087, 2007.
18. Dean, D. M., Napolitano, A. P., Youssef, J., and Morgan, J. R. Rods, tori, and honeycombs: the directed self-assembly of microtissues with prescribed microscale geometries. Faseb J 21, 4005, 2007.
19. Rago, A. P., Dean, D. M., and Morgan, J. R. Controlling cell position in complex heterotypic three-dimensional microtissues by tissue fusion. Biotechnol Bioeng 102, 1231, 2009.
20. Griffith, L. G., and Naughton, G. Tissue engineering—current challenges and expanding opportunities. Science 295, 1009, 2002.
21. Kelm, J. M., Djonov, V., Ittner, L. M., Fluri, D., Born, W., Hoerstrup, S. P., and Fussenegger, M. Design of custom-shaped vascularized tissues using microtissue spheroids as minimal building units. Tissue Eng 12, 2151, 2006.
22. Du, Y., Lo, E., Ali, S., and Khademhosseini, A. Directed assembly of cell-laden microgels for fabrication of three-dimensional tissue constructs. Proc Natl Acad Sci USA 105, 9522, 2008.
23. Dean, D. M., and Morgan, J. R. Cytoskeletal-mediated tension modulates the directed self-assembly of microtissues. Tissue Eng Part A 14, 1989, 2008.
24. Krieg, M., Arboleda-Estudillo, Y., Puech, P. H., Kafer, J., Graner, F., Muller, D. J., and Heisenberg, C. P. Tensile forces govern germ-layer organization in zebrafish. Nat Cell Biol 10, 429, 2008.
25. Jakab, K., Norotte, C., Damon, B., Marga, F., Neagu, A., Besch-Williford, C. L., Kachurin, A., Church, K. H., Park, H., Mironov, V., Markwald, R., Vunjak-Novakovic, G., and Forgacs, G. Tissue engineering by self-assembly of cells printed into topologically defined structures. Tissue Eng Part A 14, 413, 2008.
26. McLaughlin, M. E., Kruger, G. M., Slocum, K. L., Crowley, D., Michaud, N. A., Huang, J., Magendantz, M., and Jacks, T. The Nf2 tumor suppressor regulates cell-cell adhesion during tissue fusion. Proc Nall Acad Sci USA 104, 3261, 2007.
27. Discher, D. E., Janmey, P., and Wang, Y. L. Tissue cells feel and respond to the stiffness of their substrate. Science 310, 1139, 2005.
28. Silverthorn, D. U. Human physiology: an integrated approach. San Francisco, Calif.: Pearson Education, Inc., 2004.
29. Foty, R. A., Pfleger, C. M., Forgacs, G., and Steinberg, M. S. Surface tensions of embryonic tissues predict their mutual envelopment behavior. Development 122, 1611, 1996.
30. Moscona, A., and Moscona, H. The dissociation and aggregation of cells from organ rudiments of the early chick embryo. J Anat 86, 287, 1952.
31. Napolitano, A. P., Dean, D. M., Man, A. J., Youssef, J., Ho, D. N., Rago, A. P., Lech, M. P., and Morgan, J. R. Scaffold-free three-dimensional cell culture utilizing micromolded nonadhesive hydrogels. Biotechniques 43, 494, 2007.

The teachings of all of the references cited herein are hereby incorporated by reference in their entirety.

We claim:

1. A method of forming a macrotissue from at least two microtissues comprising the steps of:
   (a) pre-culturing at least one monodispersion of cells that includes at least one first cell type for at least one first pre-culture time of about one hour to about fourteen days to form at least one first microtissue;
   (b) separately, pre-culturing at least one additional monodispersion of cells that includes at least one additional cell type that is different from the first cell type for at least one additional pre-culture time of about one hour to about fourteen days to form at least one additional microtissue;
   (c) thereafter, culturing the first and the additional microtissues, together, on a surface of a substrate that is non-adhesive in an area in which tissue fusion is desired so as to effect contact between the microtissues to form a macrotissue; and
   (d) determining the position of the first and the additional cell types in the macrotissue by varying first and additional pre-culture times of the first and additional microtissues, respectively, to thereby influence the position of the first and additional cell types in the macrotissue.

2. The method according to claim 1, wherein the mono-dispersion of cells that include the first cell type and the mono-dispersion of cells that include the additional cell type are pre-cultured for greater than about 1 day.

3. The method according to claim 2, wherein the mono-dispersion of cells that include the first cell type and the mono-dispersion of cells that include the additional cell type are pre-cultured for greater than about 2 days.

4. The method according to claim 3, wherein the mono-dispersion of cells that include the first cell type and the mono-dispersion of cells that include the additional cell type are pre-cultured for about seven days.

5. The method according to claim 1, wherein the shape of the microtissues are selected from the group consisting of a spheroidal shape, a toroidal shape and a honeycomb shape.

6. The method according to claim 1, wherein the first microtissue includes one cell type and the additional microtissue includes more than one cell type.

7. The method according to claim 1, wherein the first microtissue includes two or more different cell types, and the additional microtissue includes two or more different cell types.

8. The method according to claim 7, wherein the two or more different cell types of the first microtissue have self-sorted into specific positions within the first microtissue prior to culturing with the additional microtissue, and the two or more different cell types of the additional microtissue have self-sorted into specific positions within the additional microtissue prior to culturing with the first microtissue.

9. The method according to claim 1, wherein the nonadhesive substrate in which the first and the additional microtissues are cultured is a trough in which the first and additional microtissues contact each other at one point.

10. The method according to claim 1, wherein the nonadhesive substrate in which the first and the additional microtissues are cultured is a three-dimensional substrate in which the first and the additional microtissues can make single and/or multiple contacts with one another in all possible x, y and z dimensions.

11. A method of forming a porous, multi-luminal macrotissue from at least two microtissues that each include a lumen, comprising the steps of:
    (a) pre-culturing at least one monodispersion of cells that include at least one first cell type for at least one first pre-culture time of about one hour to about fourteen days to form at least one first microtissue that includes a lumen;
    (b) separately, pre-culturing at least one additional monodispersion of cells that include at least one additional cell type that is different from the first cell type for at least one additional pre-culture time of about one hour to about fourteen days to form at least one additional microtissue that includes a lumen; and
    (c) thereafter, culturing the first and the additional microtissues on a surface of a substrate that is nonadhesive in an area in which tissue fusion is desired so as to effect contact between the microtissues to form a porous, multi-luminal macrotissue.

12. The method according to claim 11, wherein the shape of the first and the additional microtissues is at least one member selected from the group consisting of toroidal shape and honeycomb shape.

13. The method according to claim 12, wherein the first cell type is different from the additional cell type.

* * * * *